(12) United States Patent
Goodyear et al.

(10) Patent No.: US 12,005,039 B2
(45) Date of Patent: Jun. 11, 2024

(54) METHODS AND COMPOSITIONS RELATING TO LIPOKINES FOR TREATING METABOLIC DISORDERS

(71) Applicant: Joslin Diabetes Center, Inc., Boston, MA (US)

(72) Inventors: Laurie J. Goodyear, Southborough, MA (US); Kristin Stanford, Columbus, OH (US)

(73) Assignee: Joslin Diabetes Center, Inc., Boston, MA (US)

( * ) Notice: Subject to any disclaimer, the term of this patent is extended or adjusted under 35 U.S.C. 154(b) by 390 days.

(21) Appl. No.: 17/080,528

(22) Filed: Oct. 26, 2020

(65) Prior Publication Data

US 2021/0161848 A1   Jun. 3, 2021

Related U.S. Application Data

(63) Continuation of application No. PCT/IB2019/053464, filed on Apr. 26, 2019.

(60) Provisional application No. 62/663,764, filed on Apr. 27, 2018.

(51) Int. Cl.
*A61K 31/201* (2006.01)
*A61P 3/04* (2006.01)
*A61P 21/06* (2006.01)

(52) U.S. Cl.
CPC .............. *A61K 31/201* (2013.01); *A61P 3/04* (2018.01); *A61P 21/06* (2018.01)

(58) Field of Classification Search
CPC ................................ A61K 31/201; A61P 3/08
See application file for complete search history.

(56) References Cited

U.S. PATENT DOCUMENTS

| | | |
|---|---|---|
| 9,675,580 B2 | 6/2017 | Kim et al. |
| 2017/0027902 A1 | 2/2017 | Robertson et al. |
| 2017/0204415 A1 | 7/2017 | Hargreaves et al. |

FOREIGN PATENT DOCUMENTS

| | | | |
|---|---|---|---|
| EP | 3122872 B1 | 7/2019 | |
| WO | WO-2012019071 A1 | 2/2012 | |
| WO | WO-2016048005 A2 | 3/2016 | |
| WO | WO-2017042267 A1 | 3/2017 | |
| WO | WO-2018142379 A1 * | 8/2018 | ........... A61K 31/201 |

OTHER PUBLICATIONS

Lynes et al., "The cold-induced lipokine 12,13-diHOME promotes fatty acid transport into brown adipose tissue," Nat. Med. 2017;23(5):631-37. PMID: 28346411. (Year: 2017).*

Burhans et al., Hepatic oleate regulates adipose tissue lipogenesis and fatty acid oxidation, Journal of Lipid Research, 2015, p. 304-318, vol. 56, Elsevier.
Cao et al., Identification of a Lipokine, a Lipid Hormone Linking Adipose Tissue to Systemic Metabolism, Cell, 2008, p. 933-944, vol. 134, issue 6, Elsevier.
Carnero et al., Randomized trial reveals that physical activity and energy expenditure are associated with weight and body composition after RYGB, Obesity (Silver Spring), 2017, p. 1206-1216, vol. 25, issue 7, PubMed.
Coen et al., Skeletal muscle mitochondrial energetics are associated with maximal aerobic capacity and walking speed in older adults, The Journals of Gerontology Series A, Biological Sciences and Medical Sciences, 2012, p. 447-455, vol. 68, issue 4, Oxford Journals.
Coen et al., Exercise and Weight Loss Improve Muscle Mitochondrial Respiration, Lipid Partitioning and Insulin Sensitivity Following Gastric Bypass Surgery, Diabetes, 2015, p. 3737-50, American Diabetes Association.
Cypress et al., Cold but not sympathomimetics activates human brown adipose tissue in vivo, Medical Sciences, 2012, p. 10001-10005, vol. 109, issue 25, PNAS.
Egan et al., Exercise metabolism and the molecular regulation of skeletal muscle adaptation, Cell Metabolism Review, 2013, p. 162-184, vol. 17, issue 2, Elsevier.
Goodyear et al., Exercise, glucose transport, and insulin sensitivity, Annual Review of Medicine, 1998, p. 235-61, vol. 49, Annual Reviews. (Abstract only).
Hayashi et al., Evidence for 5' AMP-activated protein kinase mediation of the effect of muscle contraction on glucose transport, Diabetes, 1998, p. 1369-1373, vol. 47, issue 8, Rapid Publications.
Henkin et al., Real-time noninvasive imaging of fatty acid uptake in vivo, ACS Chemical Biology, 2012, p. 1884-1891, vol. 7, issue 11, ACS Publications.
Kato et al., Oxygenated Fatty Acids with Anti-rice Blast Fungus Activity in Rice Plants Bioscience, Biotechnology, and Biochemistry, 1993, p. 283-287, vol. 57, issue 2, Oxford Academic.
Liao et al., Real-time quantification of fatty acid uptake using a novel fluorescence assay, Journal of Lipid Research, 2005, p. 597-602, vol. 46, Issue 3, American Society for Biochemistry and Molecular Biology, Inc.
Liu et al., A diurnal serum lipid integrates hepatic lipogenesis and peripheral fatty acid use, Nature, 2013, p. 550-554, vol. 502, issue 7472, Springer Nature Limited.
Lynes et al. "The cold-induced lipokine 12, 13-diHOME promotes fatty acid transport into brown adipose tissue", Nat Med. 2017. vol. 23(5), p. 631-637, entire document, especially: abstract; p. 4, para 2; p. 16, Figure 3b-3d. (Abstract only).

(Continued)

*Primary Examiner* — Theodore R. Howell
(74) *Attorney, Agent, or Firm* — Womble Bond Dickinson (US) LLP; Cristin H. Cowles; Matthew J. Powers

(57) ABSTRACT

The invention includes methods and compositions for treating a metabolic disorder, such as metabolic syndrome, hyperlipidemia and associated disorders, such as obesity and diabetes. The invention includes a method of treating a human subject comprising administering 12,13-dihydroxy-9Z-octadecenoic acid (12,13-diHOME) to the subject. The invention also includes methods and compositions for treating disorders and conditions that would benefit from skeletal muscle fatty acid uptake and oxidation, increased mitochondrial respiration in skeletal muscle and/or enhanced exercise capacity.

8 Claims, 11 Drawing Sheets

Specification includes a Sequence Listing.

(56) References Cited

OTHER PUBLICATIONS

Motiani et al., Decreased insulin-stimulated brown adipose tissue glucose uptake after short-term exercise training in healthy middle-aged men, Diabetes, Obesity & Metabolism, 2017, p. 1379-1388, vol. 19, issue 10, Wiley.

Nedachi et al., Regulation of glucose transporters by insulin and extracellular glucose in C2C12 myotubes, Endocrinology and Metabolism, 2006, p. E817-828, vol. 291, issue 4, American Journal of Physiology.

Nieman et al., Metabolomics approach to assessing plasma 13- and 9-hydroxy-octadecadienoic acid and linoleic acid metabolite responses to 75-km cycling, Regulatory Integrative and Comparative Physiology, 2014, p. R68-74, vol. 307, issue 1, American Journal of Physiology.

Pedersen et al., Muscle as an endocrine organ: focus on muscle-derived interleukin-6, Physiological Reviews, 2008, p. 1379-1406, vol. 88, American Journal of Physiology.

Pruchnic et al., Exercise training increases intramyocellular lipid and oxidative capacity in older adults, Endocrinology and Metabolism, 2004, E857-862, vol. 287, issue 5, American Journal of Physiology.

Sisemore et al., Cellular Characterization of Leukotoxin Diol-Induced Mitochondrial Dysfunction, Archives of biochemistry and biophysics, 2001, 32-37, vol. 392, issue 1, Elsevier. (Abstract Only).

Stanford et al., Exercise Effects on White Adipose Tissue: Beiging and Metabolic Adaptations, Diabetes, 2015a, p. 2361-2368, vol. 64, Issue 7, American Diabetes Association.

Stanford et al., A novel role for subcutaneous adipose tissue in exercise-induced improvements in glucose homeostasis, Diabetes, 2015b, p. 2002-2014, vol. 64, Issue 6, American Diabetes Association.

Stanford et al., Exercise regulation of adipose tissue, Adipocyte, 2016, p. 153-162, vol. 5, Issue 2, Taylor & Francis.

Stanford et al., 12,13-diHOME: An Exercise-Induced Lipokine that Increases Skeletal Muscle Fatty Acid Uptake, Cell Metabolism, 2018, vol. 27, Issue 5, pp. 1111-1120, Elsevier.

Townsend et al., Increased Mitochondrial Activity in BMP7-Treated Brown Adipocytes, Due to Increased CPT1- and CD36-Mediated Fatty Acid Uptake, Antioxidants & Redox Signaling, 2013, p. 243-257, vol. 19, Issue 3, Mary Ann Liebert, Inc.

Vernochet et al, Adipose-specific deletion of TFAM increases mitochondrial oxidation and protects mice against obesity and insulin resistance, Cell Metabolism, 2012, p. 765-776, vol. 16, Issue 6, Elsevier.

Vosselman et al., Low brown adipose tissue activity in endurance-trained compared with lean sedentary men, Nature, 2015, p. 1696-702, vol. 39, Issue 12, International Journal of Obesity.

Yore et al., Discovery of a class of endogenous mammalian lipids with anti-diabetic and anti-inflammatory effects, Cell, 2014, p. 318-332, vol. 159, Issue 2, Elsevier.

Wu et al., Thermogenic Capacity Is Antagonistically Regulated in Classical Brown and White Subcutaneous Fat Depots by High Fat Diet and Endurance Training in Rats: Impact on Whole-Body Energy Expenditure, The Journal of Biological Chemistry, 2014, p. 34129-34140, vol. 289, Issue 49, ASBMB.

WIPO, International Search Report and Written Opinion for Application No. PCT/IB2019/053464, dated Sep. 30, 2019, p. 1-11.

\* cited by examiner

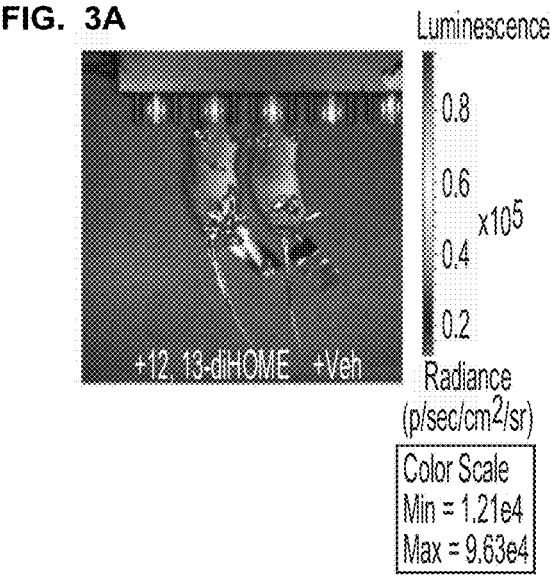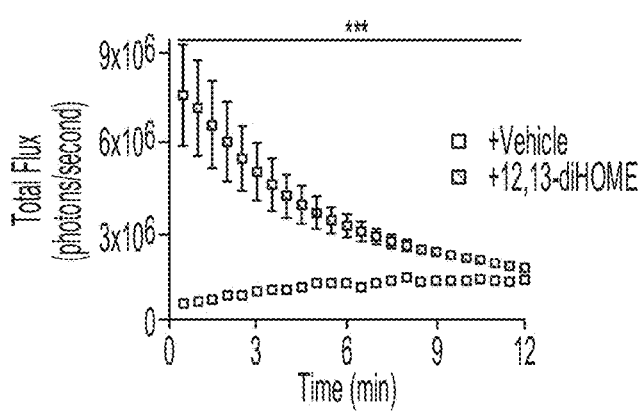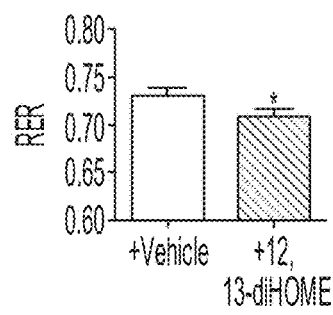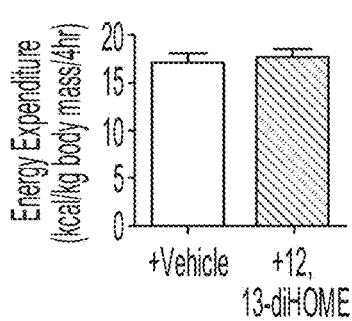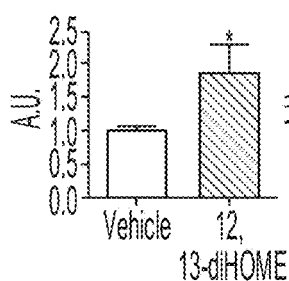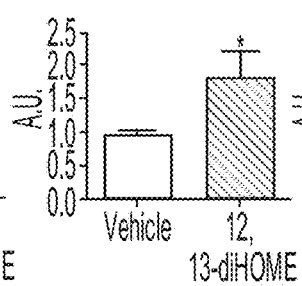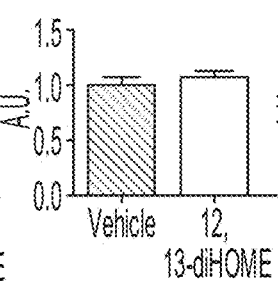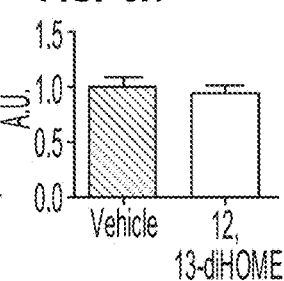

FIG. 6A
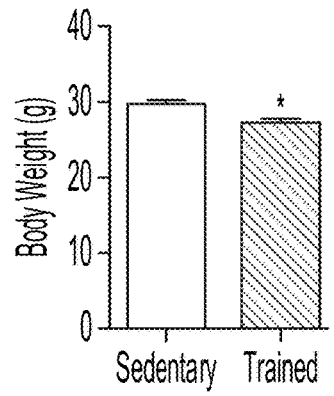
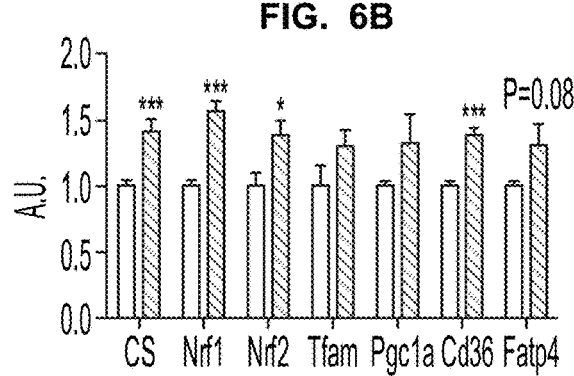
FIG. 6B
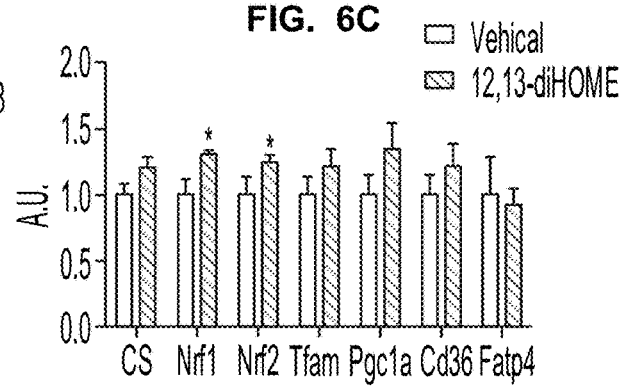
FIG. 6C
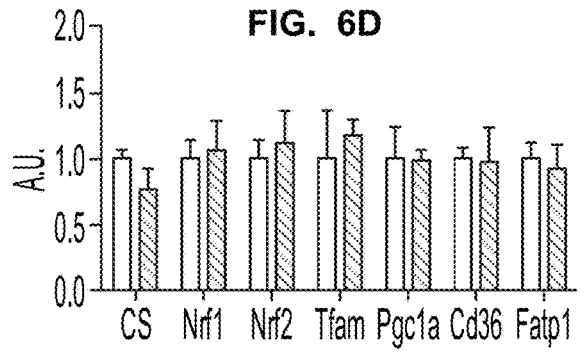
FIG. 6D
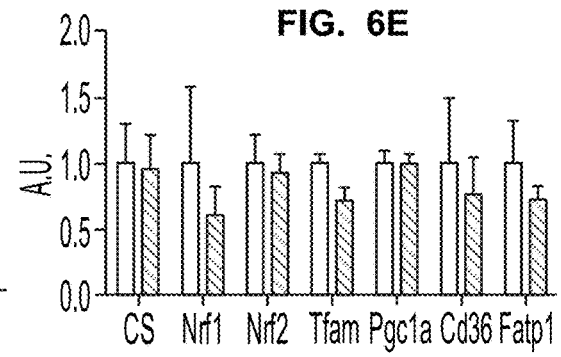
FIG. 6E
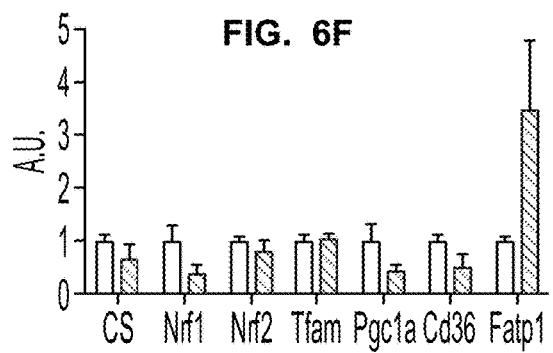
FIG. 6F
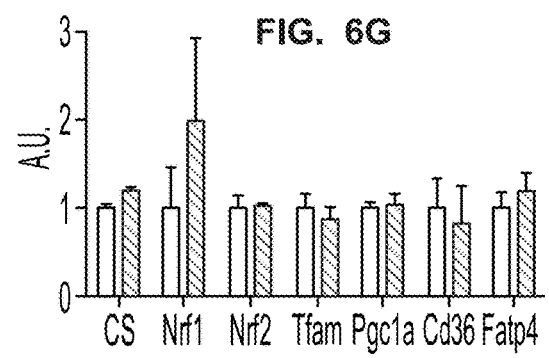
FIG. 6G

SEQUENCE LISTING

<160> NUMBER OF SEQ ID NOS: 26

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1
ggagacctta ccacttgaag atg                                              23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 2
gcccggaacc tatctatcct ct                                            22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
accactcatg gatgaaagct aca                                           23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcaggtagat tggctccaca g                                             21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagtggactc cgatagcacg                                               20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgggacgact acagagccg                                                19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tccctggtgt acggctactg                                               20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 8
atcttaaccc ggagtccttg a                                              21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aactttggca ttgtggaagg                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acacattggg ggtaggaaca                                                20

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gactacatct ggaacacact caattca                                        27

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgagggtcag tcttcctcag tac                                            23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caacagggaa gaaacggaaa                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```
gcaccacatt ctccaaaggt                                              20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggttgccca cattcccaaa caag                                         24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttgctccatg tcctgctcta tgct                                         24

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtccataggc accgtattgc                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cccatgctgg aaaaacactt                                              20

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaatcaagcc actacagaca ccg                                          23

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
catccctctt gagcctttcg tg                                              22
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
tggagctgtt attggtgcag                                                 20
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
tgggttttgc acatcaaaga                                                 20
```

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
tgccacagat cggcgagttc ta                                              22
```

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
agtggctcca tcgtgtcctc at                                              22
```

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
gacttctcca gccgtttcca ca                                              22
```

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 26
caaaggacag gatgcggcta ttg                                          23
```

METHODS AND COMPOSITIONS RELATING TO LIPOKINES FOR TREATING METABOLIC DISORDERS

RELATED APPLICATIONS

This application is a continuation of International Application No. PCT/IB2019/053464, filed on Apr. 26, 2019, which claims priority to U.S. Provisional Patent Application No. 62/663,764, filed on Apr. 27, 2018. The entire contents of the aforementioned applications are hereby incorporated by reference herein in their entirety.

GOVERNMENT INTEREST

This invention was made with Government support under grant numbers R01-DK112283, R01-DK099511, R01-HL138738 and K01-DK105109 awarded by the U.S. National Institutes of Health (NIH). The Government has certain rights in this invention.

SEQUENCE LISTING

The application contains a Sequence Listing which has been filed electronically in ASCII format and is hereby incorporated by reference in its entirety. Said ASCII copy, created on Oct. 26, 2020, is named J103021_1060US_SL.txt and is 6,214 bytes in size.

BACKGROUND OF THE INVENTION

Exercise results in adaptations to almost all tissues in the body, and these changes contribute to the beneficial effects of exercise to improve metabolic health. Even a single bout of moderate intensity exercise can have dramatic effects on glucose metabolism, lowering circulating insulin concentrations and making skeletal muscles more sensitive to insulin (Goodyear and Kahn, 1998). Exercise training, defined as repeated bouts of exercise over a period of weeks, months, or years can also result in lowering of insulin concentrations and improve glucose tolerance (Egan and Zierath, 2013; Goodyear and Kahn, 1998).

Circulating factors released from tissues during exercise have been hypothesized to mediate some of the health benefits of regular physical activity. Recently there has been great interest in identifying novel circulating factors that mediate the beneficial effects of exercise on health. However, most of this focus has been on the investigation of muscle derived factors, known as myokines (Pedersen and Febbraio, 2008).

Recently, a class of lipids, referred to as lipokines, have been identified and have been shown to act as signaling molecules that can influence systemic metabolism (Cao et al., 2008; Liu et al., 2013; Lynes et al., 2017; Yore et al., 2014). Lipokines can be released from adipose tissue (Cao et al., 2008; Lynes et al., 2017; Yore et al., 2014) and liver (Burhans et al., 2015; Liu et al., 2013) and have been reported to both improve skeletal muscle insulin sensitivity (Cao et al., 2008; Liu et al., 2013; Yore et al., 2014) or impair metabolic homeostasis (Burhans et al., 2015). However, there remains a need in the art for novel exercise-stimulated factors that contribute to and improve metabolic activity.

SUMMARY OF THE INVENTION

The present invention is based, at least in part, on the discovery that certain circulating lipokines can act as mediators that contribute to changes in metabolic activity in response to physical exercise. A described herein, 12,13-dihydroxy-9Z-octadecenoic acid (12,13-diHOME) is produced in response to a single bout of exercise, and increases skeletal muscle fatty acid uptake and oxidation, resulting in a decrease in the level of circulating triglycerides in the blood of a subject. Further, as described herein, an increase in the level of circulating 12,13-diHOME correlates with an increased capacity for mitochondrial respiration in skeletal muscle. Thus, the present invention includes methods and compositions for treating disorders and conditions that would benefit from skeletal muscle fatty acid uptake and oxidation, increased mitochondrial respiration in skeletal muscle and/or enhanced exercise capacity, such as metabolic disorders (e.g., diabetes, metabolic syndrome, insulin resistance, hyperlipidemia and disorders associated with hyperlipidemia).

In one aspect, the present invention provides methods and compositions for treating a subject having a metabolic disorder, such as diabetes (e.g., type 2 diabetes) or obesity, or a mitochondrial disorder, by administering a composition comprising a lipokine, e.g., 12,13-diHOME, to the subject. In another aspect, the present invention provides methods and compositions for treating a subject having sarcopenia or cardiovascular disease, by administering a composition comprising a lipokine, e.g., 12,13-diHOME, to the subject. In another aspect, the present invention provides methods and compositions relating to decreasing the severity of a symptom in a human subject having a mitochondrial disorder, by administering to the subject a lipokine, e.g., 12,13-diHOME. In yet another aspect, the present invention provides methods and compositions relating to increasing the respiratory capacity of a working skeletal muscle. In another aspect, the present invention provides methods and compositions relating to enhancing exercise capacity in a subject.

Accordingly, in one aspect, the invention provides a method of treating a human subject having a mitochondrial disorder, said method comprising administering an effective amount of 12,13-dihydroxy-9Z-octadecenoic acid (12,13-diHOME), a stereoisomer, a geometric isomer, or a pharmaceutically acceptable salt thereof, to a subject having a mitochondrial disorder. In one embodiment, the mitochondrial disorder is selected from the group consisting of diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), neuropathy, dementia, mitochondrial myopathy, myoclonic epilepsy with ragged red fibers (MERRF), progressive myoclonic epilepsy, mitochondrial myopathy, encephalomyopathy, lactic acidosis, stroke-like symptoms (MELAS), and mitochondrial neurogastrointestinal encephalomyopathy (MNGIE).

In another aspect, the invention provides a method of treating a human subject having a condition associated with mitochondrial dysfunction, said method comprising administering an effective amount of 12,13-dihydroxy-9Z-octadecenoic acid (12,13-diHOME), a stereoisomer, a geometric isomer, or a pharmaceutically acceptable salt thereof, to a subject having a condition associated with mitochondrial dysfunction. In one embodiment, the condition associated with mitochondrial dysfunction is selected from the group consisting of Huntington's disease, Alzheimer's disease. Parkinson's disease, bipolar disorder, schizophrenia, aging and senescence, anxiety disorders, cardiovascular disease, cancer, diabetes, sarcopenia and chronic fatigue syndrome.

In another embodiment, the condition associated with mitochondrial dysfunction is type 2 diabetes.

In another aspect, the invention provides a method of treating a human subject having cardiovascular disease, said method comprising administering an effective amount of 12,13-diHOME, a stereoisomer, a geometric isomer, or a pharmaceutically acceptable salt thereof, to a subject having cardiovascular disease.

In another aspect, the invention provides a method of treating a human subject having hypertriglyceridemia, said method comprising administering an effective amount of 12,13-diHOME, a stereoisomer, a geometric isomer, or a pharmaceutically acceptable salt thereof, to a subject having hypertriglyceridemia.

In another aspect, the invention provides a method of treating a human subject having sarcopenia, said method comprising administering an effective amount of 12,13-diHOME, a stereoisomer, a geometric isomer, or a pharmaceutically acceptable salt thereof, to a subject having sarcopenia.

In another aspect, the invention provides a method of reducing severity of a symptom in a human subject having a mitochondrial disorder, said method comprising administering an effective amount of 12,13-dihydroxy-9Z-octadecenoic acid (12,13-diHOME), a stereoisomer, a geometric isomer, or a pharmaceutically acceptable salt thereof, to a subject having a mitochondrial disorder. In one embodiment, the symptom of the mitochondrial disorder is selected from the group consisting of poor growth, loss of muscle coordination, muscle weakness, visual and hearing problems, learning disabilities, heart disease, liver disease, kidney disease, gastrointestinal disorders, respiratory disorders, neurological problems, autonomic dysfunction and dementia.

In another aspect, the invention provides a method of treating a human subject having a disorder that would benefit from an increased level of metabolic activity, said method comprising administering an effective amount of 12,13-dihydroxy-9Z-octadecenoic acid (12,13-diHOME), a stereoisomer, a geometric isomer, or a pharmaceutically acceptable salt thereof, to a subject having a disorder that would benefit from an increased level of metabolic activity. In one embodiment, the disorder that would benefit from an increased level of metabolic activity is obesity or type 2 diabetes.

In another aspect, the invention provides a method of increasing the respiratory capacity of a working skeletal muscle in a human subject, said method comprising administering an effective amount of 12,13-dihydroxy-9Z-octadecenoic acid (12,13-diHOME), a stereoisomer, a geometric isomer, or a pharmaceutically acceptable salt thereof, to the subject, thereby increasing the respiratory capacity of a working skeletal muscle.

In another aspect, the invention provides a method of enhancing exercise capacity in a human subject, said method comprising administering an effective amount of 12,13-dihydroxy-9Z-octadecenoic acid (12,13-diHOME), a stereoisomer, a geometric isomer, or a pharmaceutically acceptable salt thereof, to the subject, thereby enhancing exercise capacity.

BRIEF DESCRIPTION OF THE DRAWINGS

FIG. 1A depicts a volcano plot of 88 lipids comparing the fold induction after acute exercise to the p value; 12,13-diHOME is circled in upper right hand corner (Cohort 1, n=27). See Table 1. FIG. 1B depicts a plasma concentration of 12,13-diHOME before, immediately post, and 3 h post acute exercise (Cohort 1, n=27). Symbols represent differences vs. pre-exercise ($P<0.01$). FIG. 1C depicts the plasma concentration of 12,13-diHOME before, during and 1 h after exercise (Cohort 2, n=12). Symbols represent differences compared to: pre-exercise ($P<0.01$); immediately post-exercise (#$P<0.05$); and 15 min into exercise ($^\$P<0.05$). FIG. 1D depicts plasma concentrations of 12,13-diHOME before, during and after exercise for each individual subject (Cohort 2, n=12; n=6 male and n=6 female). FIG. 1E depicts plasma concentrations of baseline (pre-exercise) 12,13-diHOME in sedentary (n=30) vs. active (n=13) (Cohort 1 and males from Cohort 2). Symbols represent differences compared to pre-exercise values (***$P<0.001$). Plasma concentration of 12,13-diHOME before, immediately post, and 3 h post an acute bout of exercise in subjects from Cohort 1. FIG. 1F depicts a plot of concentration of 12,13-diHOME (pmol/mL plasma) as a function of YS (n=4; historical data), YA (n=6), OS (n=14), and OA (n=7). Asterisks represent differences compared to pre-exercise values (*$P<0.05$; **$P<0.01$); compared to OS at the same time point (#$P<0.05$); compared to YS at the same time point (&$P<0.05$); or compared to OA at the same time point ($^\$P<0.05$). Correlations of baseline (pre-exercise) 12,13-diHOME (pmol/mL plasma) and (FIG. 1G) $VO_{2peak}$ (n=39), (FIG. 1H) total fat mass (n=39), and (FIG. 1I) BMI (n=39). See: FIG. 5 and Table 2. Correlations of (FIG. 1J) post-exercise 12,13-diHOME (pmol/mL plasma) and BMI (n=39) and (FIG. 1K) the difference in post-exercise to pre-exercise 12,13-diHOME (pmol/mL plasma) (Δ12,13-diHOME) and BMI (n=39). Correlations include data from Cohorts 1 and 2; Young Active (YA, n=6), Older Active (OA, n=7), and Older Sedentary (OS, n=14) represent Cohort 1, while the Young Sedentary Males (YS-M, n=6) and Young Sedentary Females (YS-F, n=6) represent Cohort 2. For FIGS. 1B-1K, the data are represented as mean SEM.

FIG. 2A depicts the level of circulating 12,13-diHOME immediately post an acute bout of exercise (n=7 sedentary, n=6 acute exercise). FIG. 2B depicts the level of circulating 12,13-diHOME 24 h post an acute bout of exercise (n=4/group). FIG. 2C depicts the level of circulating 12,13-diHOME 6 h or 24 h removed from 3 weeks of exercise training (n=8 sedentary, n=6 6 h post-exercise, n=6 24 h post-exercise). See FIG. 6. Asterisks represent differences compared to sedentary mice (*$P<0.05$; $P<0.01$). FIG. 2D depicts the body weight of Sham mice and iBAT-mice prior to exercise. FIG. 2E depicts results of a glucose tolerance test showing glucose concentration (mg/dL) as a function of time in Sham mice and iBAT-mice. FIG. 2F depicts the concentration circulating 12,13-diHOME (pmol/mL plasma) in Sham mice and iBAT-mice at rest (Sham, n=4; iBAT-, n=7) and after an acute bout of exercise (Sham, n=6; iBAT-, n=6). Asterisks represent differences compared to sedentary, Sham mice (*$P<0.001$). FIG. 2G depicts gene expression of Ephx1 in sedentary mice (Sed) and after a single bout of acute exercise (Ex) in mice. FIG. 2H depicts gene expression of Ephx2 in sedentary mice (Sed) and after a single bout of acute exercise (Ex) in mice. FIG. 2I depicts gene expression of Ephx1 in sedentary mice (Sed) and after 3 weeks of exercise training (Train) in mice (n=6/group). FIG. 2J depicts gene expression of Ephx2 after 3 weeks of exercise training (Train) in mice (n=6/group). FIG. 2K depicts 12,13-diHOME concentrations measured by LC- MS/MS in BAT after 3 weeks of exercise in mice. See Table 3. Asterisks represent differences compared to sedentary (*P<0.05). For FIGS. 2A-2K, data are represented as means±s.e.m.

FIGS. 3A-3H depicts the results of studies demonstrating 12,13-diHOME enhances fatty acid uptake into skeletal muscle. FIG. 3A depicts representative images of luciferase activity in ACTAcre$^{+/-}$ Rosa(stop)Luc$^{+/-}$ injected intravenously with luciferin conjugated fatty acid and 12,13-diHOME (mouse on left) or vehicle (mouse on right). Data are representative images at 8 min. FIG. 3B depicts the quantification of luciferase activity after injection; luminescence was measured every 30 s for 15 min. (n=6/group). FIG. 3C depicts the average respiratory exchange ratio (RER) and FIG. 3D depicts energy expenditure as measured by CLAMS for 4 h at room temperature in mice acutely treated with 12,13-diHOME (n=5) or vehicle (n=4). FIGS. 3E and 3F depict fatty acid uptake (FIG. 3E) and fatty acid oxidation (FIG. 3F) measured by $^{14}$C radiolabeled palmitic acid in differentiated C2C12 cells incubated with either 12,13-diHOME or vehicle. FIGS. 3G and 3H depict fatty acid uptake (FIG. 3G) and fatty acid oxidation (FIG. 3H) measured by $^{14}$C radiolabeled palmitic acid in 3T3-L1 cells incubated with either 12,13-diHOME or vehicle. The data in FIGS. 3E-3H are normalized by protein content (n=5/group). Asterisks represent differences compared to vehicle (*P<0.05; ***P<0.00). For FIGS. 3A-3H, data are represented as means±s.e.m.

FIG. 4A depicts a bioenergetic profile of differentiated C2C12 cells treated with 12,13-diHOME or vehicle (n=5/group; asterisks represent differences compared with vehicle (*p<0.0001)). FIG. 4B depicts data representing basal OCR (pmol/min) in C2C12 cells treated with 12,13-diHOME or vehicle (n=5/group). Asterisks represent differences compared to sedentary (P<0.01, *P<0.001). FIG. 4C depicts data representing ATP turnover in C2C12 cells treated with 12,13-diHOME or vehicle (n=5/group). FIG. 4D depicts data representing maximal respiration in C2C12 cells treated with 12,13-diHOME or vehicle (n=5/group). Asterisks represent differences compared to sedentary (P<0.01, ***P<0.001). FIG. 4E depicts the average RER measured by CLAMS for 4 h at room temperature in Sham-sedentary (n=4), Sham-trained (n=4), iBAT-sedentary (n=4), iBAT-trained (n=5), or iBAT-trained acutely treated with 12,13-diHOME (n=5). Asterisks represent differences compared to Sham-sedentary mice (*P<0.05); or compared to iBAT-sedentary mice (#P<0.05). Respiration was measured in permeabilized fiber bundles by high resolution respirometry in subjects from Cohort 1. Pre-exercise 12,13-diHOME correlated with ADP stimulated respiration. FIG. 4F depicts FAO supported OXPHOS (FAO$_P$) expressed as FAO$_P$ (pmol/min/mg) as a function of 12,13-diHOME (pmols/mL plasma). FIG. 4G depicts results of an assay comparing complex I and FAO$_P$ (CI$_\&$FAO$_P$) mitochondrial expressed as CI$_\&$FAO$_P$ (pmol/min/mg) as a function of 12,13-diHOME (pmols/mL plasma). FIG. 4H depicts results of an assay comparing complex I, II and FAO supported coupled respiration (CI+II$_\&$FAO$_P$), expressed as CI+II$_\&$FAO$_P$ (pmol/min/mg) as a function of 12,13-diHOME (pmols/mL plasma). FIG. 4I depicts results of an assay comparing non-ADP stimulated (FAOL) respiration (n=27). For FIGS. 4A-4I, data are represented as means±s.e.m.

FIG. 5A depicts graphical lipidomic profiles of the relative amount of precursor lipid species, pro-inflammatory/anti-inflammatory species and the enzyme pathway involved lipid biosynthesis for all lipid species measured by LC-MS. FIGS. 5B-5D depict correlations between linoleic acid metabolites 12,13-epOME (n=39; FIG. 5B), 9,10-epOME (n=39; (FIG. 5C), and 9,10-diHOME (n=39; (FIG. 5D) and VO$_{2peak}$. FIGS. 5E-5G depict correlations between 12,13-diHOME and all subjects body weight (n=39; FIG. 5E), triglyceride levels (n=39; FIG. 5F), and glucose levels (n=39; FIG. 5G). FIGS. 5H-5J depict correlations between linoleic acid metabolites 12,13-epOME (n=39, FIG. 5H), 9,10-epOME (n=39; FIG. 5I), and 9,10-diHOME (n=39; FIG. 5I) and BMI. Data shown as: Young Active (YA, n=6), Older Active (OA, n=7), and Older Sedentary (OS, n=14) representing Cohort 1, while the Young Sedentary Males (YS-M, n=6) and Young Sedentary Females (YS-F, n=6) represent Cohort 2. The x-axis of FIGS. 5B-5J represent either 12,13-epOME or 9,10-epOME in units of pmols/mL plasma.

FIGS. 6A-6G depicts body mass after exercise and gene expression after acute injection of 12,13-diHOME. FIG. 6A graphically depicts the body mass of mice after 3 weeks of exercise training as compared to sedentary mice. Data are represented as means±s.e.m. (n=6). Asterisks represent differences compared to pre exercise (*P<0.05). FIG. 6B depicts the expression of mitochondrial and fatty acid genes in tibialis anterior (TA) skeletal muscle. FIG. 6C depicts the expression of mitochondrial and fatty acid genes in the heart. FIG. 6D depicts the expression of mitochondrial and fatty acid genes in subcutaneous white adipose tissue (scWAT). FIG. 6E depicts the expression of mitochondrial and fatty acid genes in perigonadal white adipose tissue (pgWAT). FIG. 6F depicts the expression of mitochondrial and fatty acid genes in brown adipose tissue (BAT). FIG. 6G depicts the expression of mitochondrial and fatty acid genes in liver. Data are represented as means±s.e.m. (n=4/group). Asterisks represent differences compared to pre exercise (*P<0.05; ***P<0.001).

FIG. 7A depicts $^3$H-2DG glucose uptake measured in differentiated C2C12 cells incubated with either vehicle or 12,13-diHOME. Data are represented as means±s.e.m. (n=6/group). FIG. 7B depicts $^3$H-2DG glucose uptake in isolated soleus incubated with either vehicle or 12,13-diHOME (300 ng/ml) for one hour. Data are represented as means±s.e.m. (n=6/group). FIG. 7C depicts $^3$H-2DG glucose uptake in extensor digitorum longus (EDL) incubated with either vehicle or 12,13-diHOME (300 ng/ml) for one hour. Data are represented as means±s.e.m. (n=6/group).

DETAILED DESCRIPTION

Figure 1A:
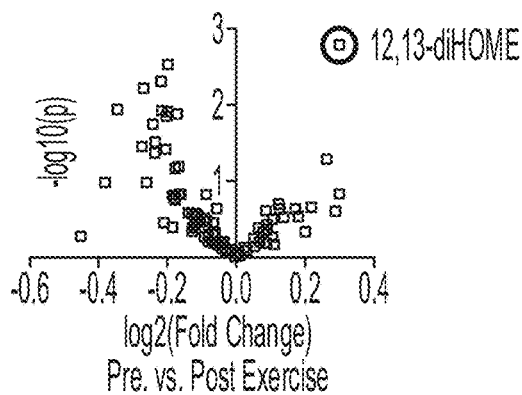
FIGS. 1A-1K depict the identification of 12, 13-diHOME, an exercise-induced lipokine.

The present invention provides, in one embodiment, methods and compositions for treating a subject having a metabolic disorder such as diabetes (e.g., type 2 diabetes) or obesity. In another embodiment, the present invention provides methods and compositions for treating a subject having a mitochondrial disorder.

Thus, the present invention provides, in certain embodiments, a method of treating a subject having a disorder or condition that would benefit from an increase in skeletal muscle fatty acid uptake and oxidation, increased capacity for mitochondrial respiration in skeletal muscle and/or enhanced exercise capacity, e.g., a metabolic disorder such as hyperlipidemia, or diabetes, by administering 12,13- diHOME, to the subject. The present invention also provides, in one embodiment, administering 12,13-diHOME to a subject in order to decrease the level of circulating triglycerides in the blood of the subject in need thereof. The present invention also provides, in one embodiment, methods and compositions for treating a subject having a disorder characterized by high level of lipids (e.g., fats, cholesterol and triglycerides) in the blood. The present invention also provides, in one embodiment, methods and compositions for treating a subject having sarcopenia or cardiovascular disease, by administering a composition comprising a lipokine, e.g., 12,13-diHOME, to the subject. The present invention also provides, in one embodiment, methods and compositions relating to decreasing the severity of a symptom in a human subject having a mitochondrial disorder, by administering to the subject a lipokine, e.g., 12,13-diHOME. The present invention also provides, in one embodiment, methods and compositions relating to increasing the respiratory capacity of a working skeletal muscle. The present invention also provides, in one embodiment, methods and compositions relating to enhancing exercise capacity in a subject.

Definitions

In order that the present invention may be more readily understood, certain terms are first defined. Unless defined otherwise, technical and scientific terms used herein have the same meaning as is commonly understood by one of skill in the art. In addition, it should be noted that whenever a value or range of values of a parameter are recited, it is intended that values and ranges intermediate to the recited values are also intended to be part of this invention.

As used herein, the term "12,13-dihydroxy-9Z-octadecenoic acid" or "12,13-diHOME," refers to a long-chain fatty acid, which is a soluble epoxide hydrolase (sEH) metabolite of 12,13-EpOME. The structure of 12, 13-diHOME is described below (I).

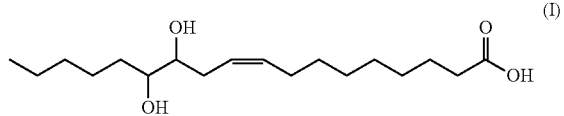 [SMILES: CCCCCC(O)C(O)C/C=C\CCCCCCCC(=O)O]

"Metabolic disorder" means a condition characterized by an alteration or disturbance in one or more metabolic processes in the body. Metabolic disorders include, but are not limited to, insulin resistance, diabetes (e.g., type 2 diabetes), obesity, metabolic syndrome, and hyperlipidemia.

"Metabolic syndrome" means a condition characterized by a clustering of lipid and non-lipid risk factors of metabolic origin. The risk factors place a subject at high risk for coronary artery disease. These conditions include Type II diabetes, central obesity also known as visceral adiposity, high blood pressure, and a poor lipid profile with elevated LDL ("bad") cholesterol, low HDL ("good") cholesterol, and elevated triglycerides.

"Mitochondrial disorder" means a disorder that is primarily caused by damaged or dysfunctional mitochondria. Metabolic disorders include, but are not limited to, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), neuropathy, dementia, mitochondrial myopathy, myoclonic epilepsy with ragged red fibers (MERRF), progressive myoclonic epilepsy, mitochondrial myopathy, encephalomyopathy, lactic acidosis, stroke-like symptoms (MELAS), and mitochondrial neurogastrointestinal encephalomyopathy (MNGIE).

As used herein, "a condition associated with mitochondrial dysfunction" is generally a condition that results in a subject as a result of a dysfunction(s) in mitochondria. Condition(s) associated with mitochondrial dysfunction include, but are not limited to, of Huntington's disease, Alzheimer's disease. Parkinson's disease, bipolar disorder, schizophrenia, aging and senescence, anxiety disorders, cardiovascular disease, cancer, diabetes, sarcopenia and chronic fatigue syndrome.

As used herein, the term "hyperlipidemia" refers to a metabolic disorder characterized by abnormally elevated levels of any or all lipids and/or lipoproteins in the blood of a subject.

The term "a disorder associated with hyperlipidemia" refers to a disease or condition in which hyperlipidemia is considered a risk factor. Examples of disorders associated with hyperlipidemia include, but are not limited to, diabetes, obesity, heart disease, and atherosclerosis.

As used herein, the term "total cholesterol level" refers to a measure of the total amount of cholesterol in the blood, i.e., the combination of low-density lipoprotein (LDL) cholesterol level, high-density lipoprotein (HDL) cholesterol level, and triglyceride level.

As used herein, the term "triglyceride" refers to lipids that are composed of a glycerol esterified to 3 fatty acid chains of varying length and composition.

As used herein, the term "triglycerides in the circulation" or "circulating triglycerides" refers to triglycerides in the blood, plasma, or serum of a subject.

As used herein, the term "cardiovascular disease" or "heart disease" refers to a disease affecting the blood vessels or heart, which includes, for example, arteriosclerosis, coronary artery disease (or narrowing of the arteries), heart valve disease, arrhythmia, heart failure, hypertension, orthostatic hypotension, shock, endocarditis, diseases of the aorta and its branches, disorders of the peripheral vascular system, heart attack, cardiomyopathy, and congenital heart disease.

"Diabetes" or "diabetes mellitus" means a disease in which the body does not produce or properly use insulin, resulting in abnormally high blood glucose levels. In certain embodiments, diabetes is type 1 diabetes. In certain embodiments, diabetes is type 2 diabetes.

"Prediabetes" means a condition in which a subject's blood glucose levels are higher than in a subject with normal blood glucose levels but lower but not high enough for a diagnosis of diabetes.

"Type 2 diabetes" means diabetes characterized by insulin resistance and relative insulin deficiency (also known as diabetes mellitus type 2, and formerly called diabetes mellitus type 2, non-insulin-dependent diabetes (NIDDM), obesity related diabetes, or adult-onset diabetes).

"Obesity" means an excessively high amount of body fat or adipose tissue in relation to lean body mass. The amount of body fat (or adiposity) includes both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. "Overweight" refers to individuals with a BMI of 25 to 30, as defined by the Center for Disease Control and Prevention.

"Steatosis" means a condition characterized by the excessive accumulation of triglycerides in hepatocytes.

As used herein, the term "treating" a disease or disorder means reversing, alleviating, ameliorating, inhibiting, slowing down or stopping the progression, aggravation, deterioration, or severity of a condition associated with such a disease or disorder, but not necessarily requiring a complete treatment or prevention of the disease or disorder. In one embodiment, the symptoms of a disease or disorder are alleviated by at least 5%, at least 10%, at least 20%, at least 30%, at least 40%, at least 50%, or more than 50%.

The terms "prevent" or "preventing" refer to delaying or forestalling the onset or development of a disease, disorder, or condition for a period of time from minutes to indefinitely. Prevent also means reducing risk of developing a certain disease, disorder, or condition.

"At risk for developing" means a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

The term "effective amount" or "effective dose", as used interchangeably herein, refers to any amount or dose of a compound or composition that is sufficient to fulfill its intended purpose(s), i.e., a desired biological or medicinal response in a tissue or subject at an acceptable benefit/risk ratio. In some embodiments, an "effective amount" is an amount that, when administered according to a particular regimen, produces a positive clinical outcome with a reasonably acceptable level of adverse effects (e.g., toxicity), such that the adverse effects, if present, are tolerable enough for a subject or patient to continue with the therapeutic regimen, and the benefit of the therapy overweighs risk of toxicity. In one embodiment, an effective amount is the amount of a compound that is able to decrease the plasma level of circulating triglycerides in a human subject relative to the level prior to administration of the compound.

The term "subject" refers to either a human or non-human animal. In one embodiment, a subject is a human subject. In another embodiment, the subject is a mammal.

By a "compound," is meant a chemical, be it naturally-occurring or artificially-derived. Compounds may include, for example, peptides, polypeptides, synthetic organic molecules, naturally-occurring organic molecules, nucleic acid molecules, and components or combinations thereof.

As used herein, "brown adipose tissue" or "BAT", refers to fat tissue characterized by multiple small lipid droplets and abundant mitochondria that oxidizes nutrients and generates heat.

By "increase in the level or activity" is meant a positive change in the amount or activity of a molecule (e.g., a biological marker) in a biological sample relative to a reference level or activity. The increase can be at least 5%, 10%, 25%, 50%, 75%, 80%, 100%, 200%, or even 500% or more over the level under control conditions. Similarly, a "decrease in the level or activity" is meant a negative change in the amount or activity of the molecule (e.g., a biological marker) in a biological sample relative to a reference level or activity.

The terms "sample" or "biological sample" as used herein include any biological specimen obtained from a subject. Samples may include, without limitation, whole blood, plasma, serum, red blood cells, white blood cells (e.g., peripheral blood mononuclear cells), saliva, urine, stool (i.e., feces), tears, sweat, sebum, nipple aspirate, ductal lavage, tumour exudates, synovial fluid, cerebrospinal fluid, lymph, fine needle aspirate, amniotic fluid, any other bodily fluid, cell lysates, cellular secretion products, inflammation fluid, semen and vaginal secretions. In preferred embodiments, the sample may be whole blood or a fractional component thereof such as, e.g., plasma, serum, or a cell pellet. Preferably the sample is readily obtainable by minimally invasive methods. Samples may also include tissue samples and biopsies, tissue homogenates and the like. In a preferred embodiment, the sample is a blood plasma sample.

The term "plasma" defines the colorless watery fluid of the blood that contains no cells, but in which the blood cells (erythrocytes, leukocytes, thrombocytes, etc.) are suspended, containing nutrients, sugars, proteins, minerals, enzymes, etc.

The term "quantity", "amount," or "level", as used interchangeably herein, refer to a detectable level of a biological marker, e.g., a protein, nucleic acid, lipid, or other compound in a biological sample. The terms as used herein may particularly refer to an absolute quantification of a molecule or an analyte in a sample, or to a relative quantification of a molecule or analyte in a sample, i.e., relative to another value such as relative to a reference value as taught herein, or to a range of values indicating a base-line expression of the biomarker. These values or ranges can be obtained from a single patient or from a group of patients. A level may be measured by methods known to one skilled in the art and also disclosed herein.

As used herein, the term "control level," "reference level" or "known standard level" refer to an accepted or pre-determined level of a biological marker. For example, a control level of a marker may refer to a level determined or obtained before or prior to treatment with a therapeutic agent. Alternatively, a control level may refer to a level of a biological marker prior to the onset of disease or before administration of a drug. The level of a marker may be known in the art (e.g., normal level of HDL) or may be determined in reference to a certain subject. The level of a biological marker present in a subject or population of subjects having one or more particular characteristics, e.g., the presence or absence of a particular disease or condition.

Methods and Compositions for Treating Metabolic Disorders and/or Mitochondrial Disorders Lipids called "lipokines" with signaling properties promoting insulin sensitivity and glucose tolerance have recently been identified (Cao, H., et al., *Cell*. 134, 933-944 (2008); Liu, S., et al., *Nature*. 502, 550-554 (2013); Yore, M. M., et al., *Cell*. 159, 318-332 (2014)). Brown adipocyte tissue (BAT) is a specialized lipid metabolic tissue linked to systemic metabolic homeostasis, and cold exposure activates substrate uptake and utilization in BAT in humans (Cypess, A. M., et al., *Proc. Natl. Acad Sci. U.S.A.* 109, 10001-10005 (2012). No lipokine has been identified that mediates the beneficial effects of exercise on health, however, until the current identification of 12,13-dihydroxy-9Z-octadecenoic acid, as described in the examples below. Accordingly, the invention provides a novel therapeutic approach to increase skeletal muscle fatty acid uptake and oxidation, to increase mitochondrial respiration in skeletal muscle and to enhance exercise capacity and skeletal muscle-specific lipid utilization using lipokines.

The invention is based, at least in part, on the identification of 12,13-dihydroxy-9Z-octadecenoic acid (abbreviated 12, 13-diHOME) as a mediator of metabolic activity. Specifically, 12, 13-diHOME increases skeletal muscle fatty acid uptake and oxidation and can therefore reduce circulating triglycerides in a subject. The structure of 12, 13-diHOME is provided below in structure (I):

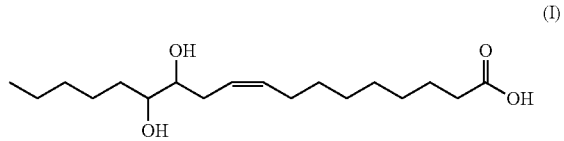 [SMILES: CCCCCC(O)C(O)C/C=C\CCCCCCCC(=O)O]

(I)

12,13-diHOME is a component of the neutrophil oxidative burst. Biosynthesis of 12,13-diHOME and its isoform 9,10-dihydroxy-12Z-octadecenoic acid (9,10-diHOME) begins via formation of 12,13-EpOME or 9,10-EpOME epoxides from linoleic acid by Cytochrome P450 (Cyp) oxidases, followed by hydrolysis catalyzed by soluble epoxide hydrolases (sEH) to form the diols 12,13-diHOME and 9,10-diHOME, respectively (as described in FIG. 5C). Synthesis methods for 12,13-diHOME are known in the art (Kato et al. (1993) Bioscience, Biotechnology, and Biochemistry, vol. 57(2) pp. 283-287).

The compound described herein (12,13-diHOME as shown in (I)) may exist in various stereoisomeric or tautomeric forms. Stereoisomers are compounds which differ only in their spatial arrangement. When a disclosed compound is named or depicted by structure without indicating stereochemistry, it is understood that the name or structure encompasses all possible stereoisomers, geometric isomers or a combination thereof.

Geometric isomers (also known as cis-trans isomerism or E-Z isomerism) are two or more coordination compounds which contain the same number and types of atoms, and bonds (i.e., the connectivity between atoms is the same), but which have different spatial arrangements of the atoms.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geometric isomers in the mixture.

The compound described herein (12, 13-diHOME as shown in (1)) has two chiral centers. Thus, it may exist in diastereoisomeric forms. For each chiral center, it exists two enantiomeric forms and the present invention includes both enantiomers and mixtures of enantiomers, such as racemic mixtures.

Racemic mixture means 50% of one enantiomer and 50% of is corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds (12, 13-diHOME as shown in (I)) disclosed herein. Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts), alkaline earth metal salts (such as magnesium and calcium salts), lysine salts and arginine salts. These salts may be prepared by methods known to those skilled in the art.

As described herein, the present invention is based, at least in part, on the discovery that certain lipokines, e.g., 12,13-diHOME can mediate metabolic activity. Thus, the level of circulating triglycerides in the blood of a subject can be decreased by administering an effective amount of 12,13-diHOME. In one embodiment, the invention provides a method of decreasing circulating levels of triglycerides and/or increasing metabolic activity in a subject in need thereof. High triglyceride levels can be associated with diabetes, kidney disease, and the use of some medications. A standard blood test can reveal whether a subject's triglycerides fall into a healthy range. Normal is defined as generally defined as being less than 150 milligrams per deciliter (mg/dL), or less than 1.7 millimoles per liter (mmol/L). Marginally high levels are considered 150 to 199 mg/dL (1.8 to 2.2 mmol/L), high levels are considered 200 to 499 mg/dL (2.3 to 5.6 mmol/L), and very high is considered 500 or more mg/dL. Thus, in one embodiment, an effective amount of 12,13-diHOME, a stereoisomer, a geometric isomer, or a pharmaceutically acceptable salt thereof, is administered to a subject having a triglyceride level over 150 mg/dL, such that the level of triglycerides in the subject is reduced to less than 150 mg/dL or is reduced at least 5%, at least 10%, at least 20%, at least 30%, at least 40%, or more than 40% of an initial level. Further, once the triglyceride level is reduced in a subject, 12,13-diHOME may be administered to a subject in need thereof in order to maintain a desired level of triglycerides. 12,13-diHOME may be also administered to increase skeletal muscle fatty acid uptake and oxidation, to increase mitochondrial respiration in skeletal muscle and to enhance exercise capacity.

Modulating the metabolic activity of a subject by modulating the levels of 12,13-diHOME can alter the level of circulating triglycerides in the blood of a subject, while increasing the capacity for metabolic respiration in skeletal muscle, which serves to treat or prevent metabolic disorders, such as metabolic syndrome, hyperlipidemia and other diseases and conditions associated with elevated lipid levels. Further, modulating the metabolic activity of a subject by modulating the levels of 12,13-diHOME can serve to treat or prevent metabolic disorders that would benefit from increased energy consumption, e.g., obesity, diabetes, atherosclerosis, cardiovascular disease and metabolic syndrome.

In one embodiment, the invention provides a method of treating a subject having a disorder that would benefit from a decreased level of circulating triglycerides. Examples of a disorder that would benefit from decreased level of circulating triglycerides include, but are not limited to, hyperlipidemia, obesity, diabetes, atherosclerosis, heart disease, and metabolic syndrome. In one embodiment, methods of treating a disorder that would benefit from a decreased level of circulating triglycerides include decreasing the level of circulating triglycerides in a subject in need thereof by administering 12,13-diHOME to a subject in need thereof. In another embodiment, the invention provides a method of treating a subject having a disorder that would benefit from an increased level of metabolic activity. In on embodiment, a disorder that would benefit from an increased level of metabolic activity is obesity. In another embodiment, a disorder that would benefit from an increased level of metabolic activity is type 2 diabetes.

Mitochondrial Disorders

In one embodiment, the invention provides a method of treating a mitochondrial disorder comprising administering 12, 13-diHOME to a subject in need thereof. Thus, the invention includes a method of treating a human subject having a mitochondrial disorder comprising administering an effective amount of 12,13-diHOME, a stereoisomer, a geometric isomer, or a pharmaceutically acceptable salt thereof, to a subject having a metabolic disorder.

Mitochondrial disorders are disorders that are primarily caused by damaged or dysfunctional mitochondria. Examples of metabolic disorders include, but are not limited to, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), neuropathy, dementia, mitochondrial myopathy, myoclonic epilepsy with ragged red fibers (MERRF), progressive myoclonic epilepsy, mitochondrial myopathy, encephalomyopathy, lactic acidosis, stroke-like symptoms (MELAS), and mitochondrial neurogastrointestinal encephalomyopathy (MNGIE). Mitochondrial disorders are often worse when the defective mitochondria are present in the muscles, cerebrum, or nerves. Therefore, the administration of an effective amount of 12,13-diHOME, a stereoisomer, a geometric isomer, or a pharmaceutically acceptable salt thereof, may ameliorate a mitochondrial disorder(s). Mitochondrial disorders may be often characterized by symptoms that include, but are not limited to, poor growth, loss of muscle coordination, muscle weakness, visual and hearing problems, learning disabilities, heart disease, liver disease, kidney disease, gastrointestinal disorders, respiratory disorders, neurological problems, autonomic dysfunction and dementia. Therefore, the administration of an effective amount of 12,13-diHOME, a stereoisomer, a geometric isomer, or a pharmaceutically acceptable salt thereof, may reduce symptom severity or relieve a symptom(s) associated with a mitochondrial disorder. Acquired conditions associated with mitochondrial dysfunction or a mitochondrial disorder may include, but are not limited to, Huntington's disease, Alzheimer's disease, Parkinson's disease, bipolar disorder, schizophrenia, aging and senescence, anxiety disorders, cardiovascular disease, cancer, diabetes, sarcopenia and chronic fatigue syndrome.

Therefore, the administration of an effective amount of 12,13-diHOME, a stereoisomer, a geometric isomer, or a pharmaceutically acceptable salt thereof, may ameliorate an acquired condition associated with mitochondrial dysfunction or a mitochondrial disorder. Defects in nuclear-encoded mitochondrial genes are also known to be associated many clinical disease phenotypes including, but not limited to, anemia, dementia, hypertension, lymphoma, retinopathy, seizures, and neurodevelopmental disorders. Therefore, the administration of an effective amount of 12,13-diHOME, a stereoisomer, a geometric isomer, or a pharmaceutically acceptable salt thereof, may ameliorate certain clinical disease phenotypes.

Metabolic Disorders

In one embodiment, the invention provides a method of treating a metabolic disorder comprising administering 12, 13-diHOME to a subject in need thereof. Thus, the invention includes a method of treating a human subject having a metabolic disorder comprising administering an effective amount of 12,13-diHOME, a stereoisomer, a geometric isomer, or a pharmaceutically acceptable salt thereof, to a subject having a metabolic disorder.

Metabolic disorders are characterized by one or more abnormalities in metabolic function in the body. Metabolic disorders affect millions of people worldwide, and can be life-threatening disorders. Examples of metabolic disorders which may be treated using the methods and compositions disclosed herein include, but are not limited to, obesity, diabetes, metabolic syndrome, hyperlipidemia, disorders associated with hyperlipidemia, and insulin resistance. Thus, the methods and compositions of the invention may be used to treat a metabolic disorder by increasing energy consumption in cells or tissue of a subject in need thereof, attained through increasing metabolic activity in the cells or tissue of the subject.

Metabolic Syndrome

In one embodiment, the invention provides a method of treating metabolic syndrome comprising administering 12, 13-diHOME to a subject in need thereof. Thus, the invention includes a method of treating a human subject having metabolic syndrome comprising administering an effective amount of 12,13-diHOME, a stereoisomer, a geometric isomer, or a pharmaceutically acceptable salt thereof, to a subject having metabolic syndrome.

Metabolic syndrome is defined as a clustering of lipid and non-lipid cardiovascular risk factors of metabolic origin. The National Cholesterol Education Program (NCEP) Adult Treatment Panel m (ATPIII) established criteria for diagnosis of metabolic syndrome when three or more of five risk determinants are present. The five risk determinants are abdominal obesity (waist circumference of greater than 102 cm for men or greater than 88 cm for women, triglyceride levels greater than or equal to 150 mg/dL tor being on medicine to treat high triglycerides), a low HDL level (HDL cholesterol levels of less than 40 mg/dL, for men and less than 50 mg/dL for women (or being on medicine to treat low HDL cholesterol), high blood pressure. i.e., blood pressure greater than or equal to 130/85 mm Hg (or being on medicine to treat high blood pressure), and high fasting glucose levels, i.e., levels greater than 100 mg/dL. These determinants can be readily measured in clinical practice (JAMA, 2001 285:2486-2497). The methods and compositions of the invention can be used to treat metabolic syndrome Hyperlipidemia Hyperlipidemia is a disorder characterized by a high level of lipids (e.g., fats, cholesterol and triglycerides) in the blood. Blood tests are conducted to determine whether a subject has hyperlipidemia. Generally, hyperlipidemia is diagnosed using a blood test and determining whether the lipid and triglyceride levels of the subject are within a normal range, including determining the levels of any one of low density lipoprotein (LDL), high density lipoprotein (HDL), total cholesterol, and triglycerides. In one embodiment, hyperlipidemia is characterized as having at least one of the following as determined using a standard blood test for a subject: an LDL cholesterol level which is 130 mg/dL or more, an HDL cholesterol level which is 50 mg/dL or less, a total cholesterol level of 200 mg/dL or more, and a triglyceride level of 150 mg/dL or more.

In one embodiment, die subject having hyperlipidemia has a total cholesterol level of about 200 mg/dL to about 400 mg/dL or more. In one embodiment, the subject has a total cholesterol level greater than 200 mg/dL, greater than 210 mg/dL, greater than 220 mg/dL, greater than 230 mg/dL, greater than 240 mg/dL, greater than 250 mg/dL, greater than 260 mg/dL, greater than 270 mg/dL, greater than 280 mg/dL, or greater than 300 mg/dL.

In one embodiment, the subject having hyperlipidemia has a circulating triglyceride level greater than 150 mg/dL to about 500 mg/dL or more. In one embodiment, the subject has a circulating triglyceride level greater than 150 mg/dL, greater than 175 mg/dL, greater than 200 mg/dL, greater than 225 mg/dL, greater than 250 mg/dL, greater than 275 mg/dL, greater than 300 mg/dL, greater than 325 mg/dL, greater than 350 mg/dL, greater than 375 mg/dL, greater than 400 mg/dL, greater than 425 mg/dL, greater than 450 mg/dL, greater than 475 mg/dL, or greater than 500 mg/dL.

Hyperlipidemia can result from primary or secondary causes. Primary hyperlipidemia is generally caused by genetic defects, and secondary hyperlipidemia generally caused by secondary factors such as disease, drugs and/or dietary factors. Hyperlipidemia can also result from a combination of primary and secondary causes.

In one embodiment, the invention includes administering an effective amount of 12,13-diHOME to a subject having hyperlipidemia, wherein the effective amount of 12,13-diHOME is an amount that decreases the level of circulating triglycerides in the blood of the subject having hyperlipidemia relative to a level of circulating triglycerides prior to treatment of the subject with 12,13-diHOME or reducing the level by at least 5%. Alternatively, if the subject is already being treated and has achieved an improved level of circulating triglycerides, then 12,13-diHOME can be administered to maintain the reduced level of triglycerides.

In one embodiment, the invention provides a method of treating hyperlipidemia comprising administering 12, 13-diHOME to a subject in need thereof. Thus, the invention includes a method of treating a human subject having hyperlipidemia comprising administering an effective amount of 12,13-diHOME, a stereoisomer, a geometric isomer, or a pharmaceutically acceptable salt thereof, to the subject having hyperlipidemia.

In one embodiment, the invention includes administering 12,13-diHOME to a subject for treating a disorder associated with hyperlipidemia. Examples of disorders associated with hyperlipidemia include, but are not limited to, obesity, diabetes, atherosclerosis, and heart disease. Thus, the methods and compositions of the invention may be used to treat a cardiovascular disease, obesity, or atherosclerosis, by increasing energy consumption in cells or tissue of a subject.

Insulin Resistance

The methods and compositions described herein may also be used to treat a subject having insulin resistance. In one embodiment, the methods of the invention include treating a subject having insulin resistance by decreasing the level of circulating triglycerides in the blood of the subject by administering an effective amount of 12,13-diHOME to the subject.

One of the main functions of insulin is to lower blood glucose levels. A subject whose cells are sensitive to the effects of insulin needs only a relatively small amount of insulin to keep blood glucose levels in the normal range. A subject who is insulin resistant requires more insulin to get the same blood glucose-lowering effects. Insulin resistance may cause hyperinsulinemia. Hyperinsulinemia may be associated with high blood pressure, heart disease and heart failure, obesity (particularly abdominal obesity), osteoporosis, and certain types of cancer, such as colon, breast and prostate cancer.

Insulin resistance can be determined using common methods known in the art. For example, a glucose tolerance test, A1c test, and/or a lipid profile (measuring the HDL, LDL, triglycerides, and total cholesterol) of a subject may be used to determine if the subject has insulin resistance. In addition, a homeostatic model assessment (HOMA) of the subject may be performed to determine if the subject has insulin resistance. The HOME test involves measuring glucose and insulin levels and then using a calculation to estimate function of the beta cells in the pancreas that produce insulin and insulin sensitivity.

In one embodiment, the invention provides a method of treating insulin resistance comprising administering 12, 13-diHOME to a subject in need thereof. Thus, the invention includes a method of treating a human subject having insulin resistance comprising administering an effective amount of 12,13-diHOME, a stereoisomer, a geometric isomer, or a pharmaceutically acceptable salt thereof, to a subject having insulin resistance.

Obesity

The methods and compositions described herein may also be used to treat a subject having obesity. In one embodiment, the methods of the invention include treating a subject having obesity by decreasing the level of circulating triglycerides in the blood of the subject by administering an effective amount of 12,13-diHOME to the subject.

Obesity is a condition characterized by an excessively high amount of body fat or adipose tissue in relation to lean body mass of a subject. The amount of body fat (or adiposity) includes both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. Overweight subject are considered having a BMI of 25 to 30, as defined by the Center for Disease Control and Prevention.

In one embodiment, methods and compositions of the invention may be used to treat obesity, by providing a means to control weight in the subject in need thereof by increasing energy consumption in cells or tissue of a subject.

Thus, 12,13-diHOME may be used to treat metabolic disorders, including insulin resistance, hyperlipidemia, diabetes, disorders associated with hyperlipidemia, obesity, and metabolic syndrome. In certain embodiments, the invention provides a method of preventing such disorders by administering 12,13-diHOME to a subject at risk for developing a metabolic disorder.

In one embodiment, the effective amount of 12,13-diHOME used to treat a metabolic disorder in a subject is an amount that decreases the level of circulating triglycerides in the blood of the subject relative to a level of circulating triglycerides prior to treatment of the subject with 12,13-diHOME. Alternatively, the effective amount may be an amount which maintains a desirable level of circulating triglycerides in the blood of a subject, e.g., maintains a level of less than 150 mg/dL of circulating triglycerides.

In one embodiment, administration of an effective amount of 12,13-diHOME may decrease the level or amount of circulating triglycerides in the blood of a subject by at least about 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 250-fold, 300-fold, 350-fold or 400-fold relative to a level of circulating triglycerides prior to treatment of the subject with 12,13-diHOME. Ranges within one or more of the preceding values e.g., about 2-fold to about 4-fold, about 3-fold to about 6-fold, about 5-fold to about 10-fold, about 8-fold to about 30-fold, about 20-fold to about 50-fold, about 40-fold to about 100-fold, about 50-fold to about 200-fold, about 200-fold to about 400-fold or about 2-fold to about 400-fold are contemplated by the invention.

Typical modes of administration of 12,13-diHOME include parenteral (e.g., intravenous, subcutaneous, intraperitoneal, intramuscular) injection or oral administration. In one embodiment, 12,13-diHOME is administered by injection. In another embodiment, the injection is subcutaneous. In a particular embodiment, the injection is into an adipose tissue.

In one embodiment, 12,13-diHOME is administered at a dose of about 0.5 mg/kg to about 300 mg/kg to a human subject. In one embodiment, 12,13-diHOME is administered at a dose of about 1 mg/kg, 2 mg/kg, 3 mg/kg, 4 mg/kg, 5 mg/kg, 10 mg/kg, 20 mg/kg, 30 mg/kg, 40 mg/kg, 50 mg/kg, 100 mg/kg, 150 mg/kg, 200 mg/kg, 250 mg/kg, 300 mg/kg, 350 mg/kg, 400 mg/kg, 450 mg/kg or 500 mg/kg. Ranges within one or more of the preceding values, e.g., about 1 mg/kg to about 5 mg/kg, about 2 mg/kg to about 10 mg/kg, about 6 mg/kg to about 40 mg/kg, about 20 mg/kg to about 100 mg/kg, about 50 mg/kg to about 200 mg/kg, about 100 mg/kg to about 400 mg/kg or about 1 mg/kg to about 500 mg/kg are contemplated by the invention.

In certain embodiments, 12,13-diHOME is administered to a subject in need thereof in combination with an additional therapeutic agent. For example, 12,13-diHOME can be administered to a subject in need in combination with a cholesterol lowering agent, such as a statin (e.g., Altoprev or Mevacor (lovastatin). Crestor (rosuvastatin), Lescol (fluvastatin), Lipitor (atorvastatin), Livalo (pitavastatin), Pravachol (pravastatin), and Zocor (simvastatin)), a bile acid binding drug (e.g., Colestid (colestipol), Prevalite (cholestyramine), and WelChol (colesevelam)), and/or a cholesterol absorption drug, (such as Zetia (ezetimibe)). In one embodiment, 12,13-diHOME is administered to a subject in need in combination with a triglyceride lowering agent, such as, but not limited to, a fibrate (e.g., Lopid (gemfibrozil), TriCor (fenofibrate)), an omega-3 fatty acid supplement, and niacin.

In addition, 12,13-diHOME may be administered in combination with a diabetic therapy and/or a HMG-CoA reductase inhibitor. Exemplary diabetic therapies are known in the art and include, for example, insulin sensitizers, such as biguanides (e.g., metformin) and thiazolidinediones (e.g., rosiglitazone, pioglitazone, troglitazone); secretagogues, such as the sulfonylureas (e.g., glyburide, glipizide, glimepiride, tolbutamide, acetohexamide, tolazamide, chlorpropamide, gliclazide, glycopyamide, gliquidone), the non-sulfonylurea secretagogues, e.g., meglitinide derivatives (e.g., repaglinide, nateglinide); the dipeptidyl peptidase IV inhibitors (e.g., sitagliptin, saxagliptin, linagliptin, vildagliptin, allogliptin, septagliptin); alpha-glucosidase inhibitors (e.g., acarbose, miglitol, voglibose); amylinomimetics (e.g., pramlintide acetate); incretin mimetics (e.g., exenatide, liraglutide, taspoglutide); insulin and its analogues (e.g., rapid acting, slow acting, and intermediate acting), bile acid sequestrants (e.g., colesevelam); and dopamine agonists (e.g., bromocriptine), alone or in combinations. Exemplary HMG-CoA reductase inhibitors include atorvastatin (Pfizer's Lipitor®/Tahor/Sortis/Torvast/Cardyl), pravastatin (Bristol-Myers Squibb's Pravachol, Sankyo's Mevalotin/Sanaprav), simvastatin (Merck's Zocor®/Sinvacor, Boehringer Ingelheim's Denan, Banyu's Lipovas), lovastatin (Merck's Mevacor/Mevinacor, Bexal's Lovastatina, Cepa; Schwarz Pharma's Liposcler), fluvastatin (Novartis' Lescol®/Locol/Lochol, Fujisawa's Cranoc, Solvay's Digaril), cerivastatin (Bayer's Lipobay/GlaxoSmithKline's Baycol), rosuvastatin (AstraZeneca's Crestor®), and pitivastatin (itavastatin/risivastatin) (Nissan Chemical, Kowa Kogyo, Sankyo, and Novartis).

In certain embodiments, the subject who is treated using the methods disclosed herein, is characterized as having a certain metabolic characteristic(s). As described below in the examples, certain metabolic indicators have been identified as having a negative correlation to plasma levels of 12,13-diHOME, including plasma triglyceride level, cholesterol level, plasma alanine transaminase (ALAT) level, Body Mass Index (BMI), Homeostatic Model Assessment of Insulin Resistance (HOMA-IR) score, plasma aspartate transaminase (ASAT) level, leptin level, and plasma gGT level. Alanine transaminase (ALAT) is also known in the art as alanine aminotransferase (ALT) or serum glutamic pyruvic transaminase (SGPT). Aspartate transaminase (ASAT) is also known in the art as aspartate aminotransferase (AST) or serum glutamic oxaloacetic transaminase (SGOT).

Methods for determining these metabolic characteristics are known in the art and can be used to identify subjects who would benefit from 12,13-diHOME therapy. In one embodiment, the methods and compositions disclosed herein are used to treat a human subject having a plasma triglyceride level greater than 1.7 mmol/l. Standard blood tests can be performed to determine a subject's plasma triglyceride level.

In one embodiment, the methods and compositions disclosed herein are used to treat a human subject having an ALAT level greater than 0.6 µkat/l. An alanine aminotransferase (ALT) or (ALAT) test, which is also known as serum glutamic pyruvic transaminase (SGPT) test, measures the amount of this enzyme in the blood and is a commonly used test to check liver function. ALAT is measured to determine if the liver of a subject is damaged or diseased. Low levels of ALAT are normally found in the blood. But when the liver is damaged or diseased, it releases ALAT into the bloodstream, which makes ALAT levels go up. Standard blood tests can be performed to determine a subject's ALAT level.

In one embodiment, the methods and compositions disclosed herein are used to treat a human subject having a BMI of 25 or more. In a separate embodiment, the methods and compositions disclosed herein are used to treat a human subject having a BMI of 30 or more (obese).

In one embodiment, the methods and compositions disclosed herein are used to treat a human subject having a HOMA-IR score of 1.9 or more. Homeostatic model assessment (HOMA) is a method for assessing β-cell function and insulin resistance (IR) from basal (fasting) glucose and insulin or C-peptide concentrations. HOME-IR scores are rated as follows: Healthy Range: 1.0 (0.5-1.4); Less than 1.0 means a subject is insulin-sensitive; above 1.9 indicates early insulin resistance; above 2.9 indicates significant insulin resistance. HOMA-IR is determined as follows: (fasting serum insulin (μU/ml)×fasting plasma glucose (mmol 1-1)/ 22.5) (Matthews et al. (1985) *Diabetologia*. 28: 412-419).

In one embodiment, the methods and compositions disclosed herein are used to treat a human subject having a plasma aspartate aminotransferase (ASAT) level of greater than 0.3 μkat/l for a male subject or a plasma ASAT level of greater than 0.6 μkat/l for a female subject.

An aspartate aminotransferase (AST) or (ASAT) test, which is also known as serum glutamic oxaloacetic transaminase (SGOT) test, measures the amount of this enzyme in the blood and is a commonly used test to check liver function. ASAT is normally found in red blood cells, liver, heart, muscle tissue, pancreas, and kidneys. ASAT levels can be determined using standard methods known in the art.

In one embodiment, the methods and compositions disclosed herein are used to treat a human subject having a plasma gGT level of 0.9 μkat/l or greater for a male subject or a plasma gGT level of 0.6 μkat/l or greater for a female subject. gGT levels can be determined using a standard blood test, where the normal range for adults is 8 to 65 U/L.

In one embodiment, the methods and compositions disclosed herein are used to treat a human subject having a plasma leptin level of 40 ng/ml or more. In one embodiment, the subject is characterized as having leptin resistance. Leptin levels can be determined using standard blood testing methods known in the art.

Thus, in certain embodiments, 12, 13-diHOME is administered to a subject having a metabolic disorder who is also characterized as having at least one of the following characteristics: a plasma ALAT level greater than 0.6 μkat/l; a BMI of 30 or more; a HOMA-IR score of 1.9 or more; a plasma triglyceride level greater than 1.7 mmol/l; a plasma ASAT level of greater than 0.3 μkat/l for a male subject or a plasma ASAT level of greater than 0.6 μkat/l for a female subject; a plasma leptin level of 40 ng/ml or more; or a plasma gGT level of 0.9 μkat/l or greater for a male subject or a plasma gGT level of 0.6 μkat/l or greater for a female subject.

Pharmaceutical Formulations

Pharmaceutical formulations comprising 12,13-diHOME may be prepared according to methods known in the art to include physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween™, Pluronics™ or polyethylene glycol (PEG).

The formulations to be used for in vivo administration must be sterile. This is readily accomplished by filtration through sterile filtration membranes.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration. In an alternative embodiment, one or more of the pharmaceutical compositions of the invention is supplied in liquid form in a hermetically sealed container indicating the quantity and concentration of the agent.

The active agent can be incorporated into a pharmaceutical composition suitable for parenteral administration, typically prepared as an injectable solution. The injectable solution can be composed of either a liquid or lyophilized dosage form in a flint or amber vial, ampule or pre-filled syringe. The liquid or lyophilized dosage may further comprise a buffer (e.g., L-histidine, sodium succinate, sodium citrate, sodium phosphate or potassium phosphate, sodium chloride), a cryoprotectant (e.g., sucrose trehalose or lactose, a bulking agent (e.g., mannitol), a stabilizer (e.g., L-Methionine, glycine, arginine), an adjuvant (hyaluronidase).

The compositions of this invention may be in a variety of forms. These include, for example, liquid, semi-solid and solid dosage forms, such as liquid solutions (e.g., injectable and infusible solutions), microemulsion, dispersions, liposomes or suspensions, tablets, pills, powders, liposomes and suppositories.

The preferred form depends on the intended mode of administration and therapeutic application. Typical modes of administration include parenteral (e.g., intravenous, subcutaneous, intraperitoneal, intramuscular) injection or oral administration. In a preferred embodiment, 12,13-diHOME is administered by injection. In another embodiment, the injection is subcutaneous. In a particular embodiment, the administration is into adipose tissue.

The active ingredients may also be packaged in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Pharmaceutical compositions comprising an agent described herein may also be formulated for administration to a particular tissue. For example, in certain embodiments, it may be desirable to administer the agent into adipose tissue, either in a diffuse fashion or targeted to a site (e.g., subcutaneous adipose tissue).

The invention also provides kits for the treatment and/or diagnosis of the disorders described above. Such kits include means for determining the level of 12,13-diHOME and instructions for use of the kit. For example, in particular embodiments, a kit of the invention includes means for determining the level of 12,13-diHOME. Kits of the invention can optionally contain additional components useful for performing the methods of the invention. For example, the kits may include means for obtaining and/or processing a biological sample from a subject. Means for isolating a biological sample from a subject can comprise one or more reagents that can be used to obtain a fluid or tissue from a subject, such as reagents that can be used to obtain or collect a cell or tissue sample from a subject. Means for processing a biological sample from a subject can include one or more reagents that can be used to transform a biological sample such that the level of one or more biomarkers in the sample can be determined. Such reagents can include, for example, reagents for isolating lipids from a biological sample. In preferred embodiments, the kits are designed for use with a human subject.

The invention is illustrated by the following examples, which are not intended to be limiting in any way.

EXAMPLES

The examples presented herein describe that certain circulating lipokines can act as novel mediators that contribute to changes in metabolic activity in response to physical exercise. The examples were surprising in demonstrating that certain lipokines, such as 12,13-dihydroxy-9Z-octadecenoic acid (12,13-diHOME), which is produced in response to physical exercise, increases skeletal muscle fatty acid uptake and oxidation, resulting in a decrease in the level of circulating triglycerides in the blood of a subject. The examples were also surprising in that an increase in the level of circulating 12,13-diHOME correlates with an increased capacity for mitochondrial respiration in skeletal muscle and enhanced exercise capacity. The experiments exemplify novel methods and mechanisms for increasing fatty acid uptake and oxidation in skeletal muscle, for increasing capacity for mitochondrial respiration, and/or enhancing exercise capacity through the administration of 12,13-diHOME for use in treating, for example, metabolic disorders, such as obesity, diabetes, hyperlipidemia, or metabolic syndrome. The examples provided herein are described in Stanford, et al., Cell Metabolism 27, p. 1111-1120 (2018), the contents of which are incorporated by reference in its entirety.

Materials and Methods

The following methods described herein were used in the examples described below unless otherwise specified.

Human Subjects

All participants provided written informed consent and the study protocol was approved by the Institutional Review Boards at Florida Hospital (Florida cohort) or the Joslin Diabetes Center (Massachusetts cohort). Participants from Florida cohort were all male subjects with an average age of 58.7±2.5 yr and a BMI of 24.8±0.6 kg/m² and were categorized as: Young Active (YA) 21-40 years (31.1±1.5 yr), Older Active (OA) and Older Sedentary (OS) 65-90 years (69.8±0.7 yr), with "Active" based on engaging in aerobic exercise (running, cycling, swimming) at least 3 days/wk. Subjects were classified as "Sedentary" if they performed one or less structured exercise session/wk. Objectively measured physical activity indicated that the YA group engaged in 60 min/day of vigorous physical activity and 126 min/day of moderate physical activity. The OA group engaged in 40 min/day of vigorous physical activity and 72 min/day of moderate physical activity. The OS group engaged in 1 min/day of vigorous physical activity and 24 min/day of moderate physical activity. Inclusion criteria included stable weight, non-smoker, BMI<35 kg/m², resting blood pressure ≤150 mmHg systolic and ≤95 mmHg diastolic. Exclusion criteria included inability or unwillingness to comply with the protocol, clinically significant CVD including MI within the past year, the presence of peripheral vascular disease, hepatic disease, renal disease, muscular or neuromuscular disease, hematologic/oncologic disease, peripheral neuropathy, orthopedic limitations, history of pulmonary emboli, history of alcohol or substance abuse, current use of blood thinners or any medication that can alter glucose homeostasis. Participants from the Massachusetts cohort consisted of males (n=6) and females (n=6), all who were young (29.4±0.6 year), and lean (BMI 22.5±0.8 kg/m²). There was no effect of sex or gender identity on the outcomes of the study. All subjects performed less than 150 min/week of exercise for the previous 3 months (87±16 minutes of exercise/week). Inclusion criteria included being between 18-35 years of age. BMI≥20 and ≤26 and HbA1C≤5.7%. Exclusion criteria included current dieting or weight loss efforts, heart or lung disease, acute systemic infection, currently pregnant or breast feeding, HIV/AIDS, cancer, hepatic disease, renal disease, demyelinating diseases, clinical history of hypertension (systolic >140 mmHg or diastolic >90 mmHg), type 1 or 2 diabetes, inability to exercise at 50% of predicted heat rate or taking beta-blockers.

Animals

Animal procedures were approved by the Institutional Animal Use and Care Committee at The Ohio State University and Joslin Diabetes Center. Male, 10 week old C57BL/6 mice purchased from Charles River Laboratories were fed a chow-diet (21% kcal from fat) ad libitum. Mice were housed on a 12-hour light/dark cycle (6a (ON)/6p (OFF)) at room temperature (22° C.) for all experiments. Mice were housed individually in static cages or in wheel cages (Nalgene) (Stanford et al., 2015b). For chronic exercise experiments, mice were given ad libitum access to food and water after removal from wheel cage. Any mouse that ran 10% less than the average of the trained group was excluded from analysis. For acute exercise experiments, 12 week old male C57BL/6 mice were familiarized with the treadmill (Quinton model 42) for 2 days prior to experiment. For iBAT-mice, mice were anesthetized using isofluorane. iBAT was surgically removed and the artery immediately cauterized. Sham mice underwent the same surgical procedure, but iBAT was not removed.

For experiments measuring in vivo bioluminescent fatty acid uptake in skeletal muscle, ACTA1cre$^{+/-}$ mice (Stock no. 006139) were bred with Rosa(stop)Luc$^{+/+}$ (Stock no. 005125) (Jackson Laboratory). Experiments measuring skeletal muscle glucose uptake in isolated skeletal muscle glucose uptake were performed in 6 week old, female, CD-1 IGS mice (Charles River Laboratories).

Cell Culture

Cells were housed at 37° C., 95% humidity and 5% $CO_2$. C2C12 myoblasts (ATCC; passages 4-7) were maintained in DMEM containing 10% FBS and 1% penicillin/streptomycin. Differentiation was induced by incubating the cells in DMEM containing 2% horse serum and 1% penicillin/streptomycin for 4 days. 3T3-LI adipocytes (ATCC; passages 4-7) were maintained in DMEM containing 10% FBS and 1% penicillin/streptomycin. Differentiation was induced by incubating the cells in DMEM containing 101% FBS and 1% penicillin/streptomycin with 400 ng/mL dexamethasone, 1 µg/mL insulin, and 115 µg/mL IBMX for days 0-2, 1 µg/mL insulin for days 2-4, and DMEM with 10% FBS and 1% penicillin/streptomycin only days 4-8.

Human Exercise Testing and Monitoring

For the Florida cohort, $VO_2$ peak was determined as peak aerobic capacity measured during a graded exercise protocol on an electronically braked cycle ergometer (Coen et al., 2013) and body composition was determined by Dual energy X-ray absorptiometry scan. The SenseWear® Pro Armband (BodyMedia) was used to monitor physical activity behaviors (Carnero et al., 2017). For the submaximal exercise test, participants were fasted overnight and were 48 h removed from the last exercise bout. Participants performed a 6-min warm-up of light cycling on the ergometer followed by 40 min at 70% of heart rate reserve (HRR). Heart rate, perceived exertion and blood pressure data were collected every 5 mins and indirect calorimetry measurements recorded (Parvo Medics). A fasting blood sample was drawn before exercise, immediately after, and 3 hours post-exercise. Exercise was performed at room temperature (22° C.). Vastus lateralis muscle biopsies were obtained under local anesthesia (Pruchnic et al., 2004). Permeabilized myofiber bundles (~1-3 mg each) were prepared immediately after the biopsy and mitochondrial respiration was evaluated by high-resolution respirometry (Coen et al., 2015).

For participants of the Massachusetts cohort, $VO_{2peak}$ was determined as peak aerobic capacity measured during a graded exercise modified Bruce protocol on a treadmill (Beltz et al., 2016, Bruce, 1971). For the submaximal exercise test, participants were fasted overnight and were one week removed from the determination of $VO_{2peak}$. A fasting blood sample was drawn before exercise, 15 min during exercise, immediately after, and 1 h post-exercise. Exercise was performed at room temperature (22° C.).

Mice and Exercise

Male, 10 week old C57BL/6 mice were fed a chow-diet (21% kcal from fat) ad libitum. Mice were housed individually in static cages or in wheel cages (Nalgene) (Stanford et al., 2015b). For chronic exercise experiments, mice were given ad libitum access to food and water after removal from wheel cage. For acute exercise experiments, 12 week old male C57BL/6 mice were familiarized with the treadmill (Quinton model 42) for 2 days prior to experiment. Mice underwent 40 min of treadmill exercise at 0.8 mph, 10% incline and all mice were able to successfully complete the acute bout of exercise. Both acute and chronic exercise experiments were performed at room temperature (22° C.).

Removal of iBAT

For iBAT-mice, mice were anesthetized using isofluorane. iBAT was surgically removed and the artery immediately cauterized. Sham mice underwent the same surgical procedure, but iBAT was not removed.

In Vivo Fatty Acid Uptake

For experiments measuring in vivo bioluminescent fatty acid uptake in skeletal muscle, ACTA1cre$^{+/-}$ mice (Stock no. 006139) were bred with Rosa(stop)Luc$^{+/+}$ (Stock no. 005125)(Jackson Laboratory). Male offspring carrying the cre allele were injected retro-orbitally with 1 μg/kg body weight 12,13-diHOME in 0.1% BSA PBS or methyl acetate as a vehicle and all mice were co-injected with 2 μm FFA-SS-Luc (Intrace Medical). This dose is based on the circulating concentration of 12,13-diHOME in mice that are housed at room temperature, 3 ng/mL (10 nM). After an acute bout of exercise, 12,13-diHOME increased to 10-30 ng/mL (30-100 nM). This is considerably below the reported cytotoxic dose of 100 mg/kg body weight (Sisemore et al., 2001). Mice were anesthetized and imaged (IVIS Spectrum CT) using sequential 30 second exposures for 12 min.

Metabolic Studies

For measurements of respiratory exchange ratio (RER) and energy expenditure, mice were placed in metabolic chambers and injected intravenously with 1 μg/kg body weight 12,13-diHOME in 0.1% BSA PBS or vehicle and then monitored in the Comprehensive Laboratory Animals Monitoring System (CLAMS) at room temperature (22° C.) for 4 h.

Skeletal Muscle [$^3$H]-2-Deoxyglucose Uptake

Isolated skeletal muscle glucose uptake was measured as previously described (Hayashi et al., 1998). Briefly, EDL or soleus muscles were dissected from 6 wk old female CD-1 mice, mounted, and incubated in Krebs-Ringer bicarbonate buffer (KRB) pH 7.4 containing 2 mM pyruvate for 60 min. Both EDL and soleus were incubated with vehicle or 300 ng/mL of 12,13-diHOME. Following treatment, glucose transport activity was measured for an additional 10 min.

Lipidomic Profiling

Lipidomic profiling was done as we have described in detail (Lynes et al., 2017). Briefly, a mixture of deuterium-labeled internal standards was added to aliquots of thawed serum, followed by cold methanol (MeOH) for Solid Phase Extraction (SPE). Following vortex, overnight storage at −20° C., and centrifugation, the supernatant was acidified and SPE was performed (Powell, 1999). The methyl formate fractions were collected, dried under nitrogen, reconstituted in MeOH:$H_2O$, centrifuged and the supernatant analyzed using the LC-MS/MS mediator lipidomics platform.

PCR and Cell Studies mRNA levels of were measured by quantitative RT-PCR using primers (Table 4). Fatty acid uptake and oxidation into differentiated C2C12 muscle cells and 3T3L1 adipocytes measured using $^{14}$C-labeled palmitic acid uptake and conversion of $^{14}$C-labeled palmitic acid into $CO_2$ as previously described (Townsend et al., 2013). Cells were treated with 1.5 μM 12,13-diHOME or methyl acetate vehicle for 15 min, similar to previous studies (Lynes et al., 2017). Oxygen consumption rates (OCR) were measured in starved (1 hour) C2C12 skeletal muscle cells treated with 1.5 μM 12,13-diHOME or methyl acetate vehicle for 15 min and OCR measured in 200 μM palmitate (Seahorse XF24) (Vernochet et al., 2012).

Glucose Uptake in C2C12 Cells 2-deoxyglucose uptake in C2C12 cells was measured as previously described (Nedachi and Kanzaki, 2006). Briefly, differentiated C2C12 myotubes were serum starved for 3 h in DMEM before any treatment. Cells were incubated with 12,13-diHOME (1.5 mM; 15 min) or insulin (100 nM; 15 min). After stimulation, cells were washed with buffer containing 140 mM NaCl, 20 mM Hepes-Na (pH 7.4), 5 mM KCl, 2.5 mM $MgSO_4$, and 1.0 mM $CaCl_2$. Glucose transport was determined by the addition of $^3$H-2-deoxyglucose for glucose for 10 min on ice. Cells were washed with ice-cold saline solution and harvested in 0.05 N NaOH to determine net accumulation of [$^3$H]-2-deoxyglucose (Nedachi and Kanzaki, 2006).

Quantification and Statistical Analyses

Statistics

Data are mean±SEM and significance defined as $P \leq 0.05$ and determined by Student t tests or two-way ANOVA and Bonferroni post hoc analysis. All analyses were performed using features present in GraphPad Prism (version 7; Graph-Pad Software, Inc. San Diego, CA). No statistical method was used to pre-determine sample size. Covariate analyses between 12,13-diHOME and body composition parameters were assessed using Spearman and Pearson correlation coefficients. The statistical parameters and the number of mice or human subjects used per experiment are found in the figure legends.

Figure 1B:
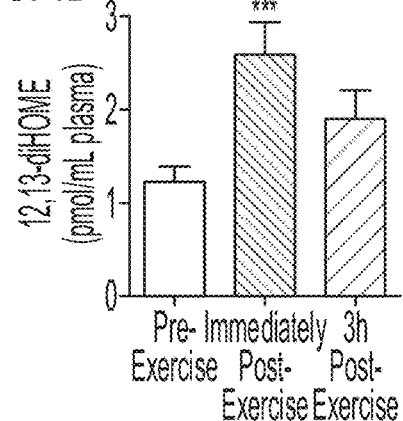
Figure 1C:
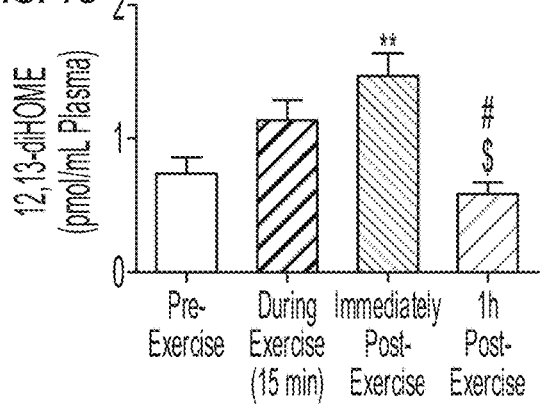
Figure 1D:
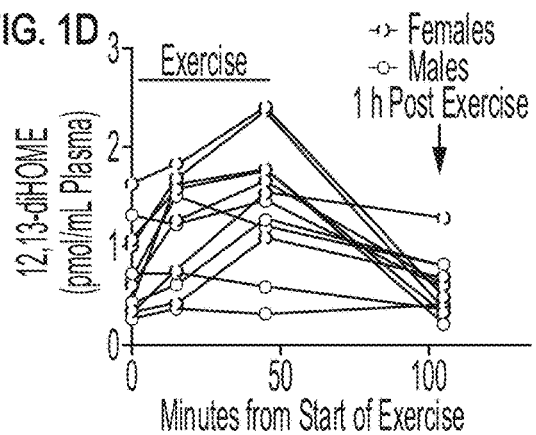
Figure 5A:
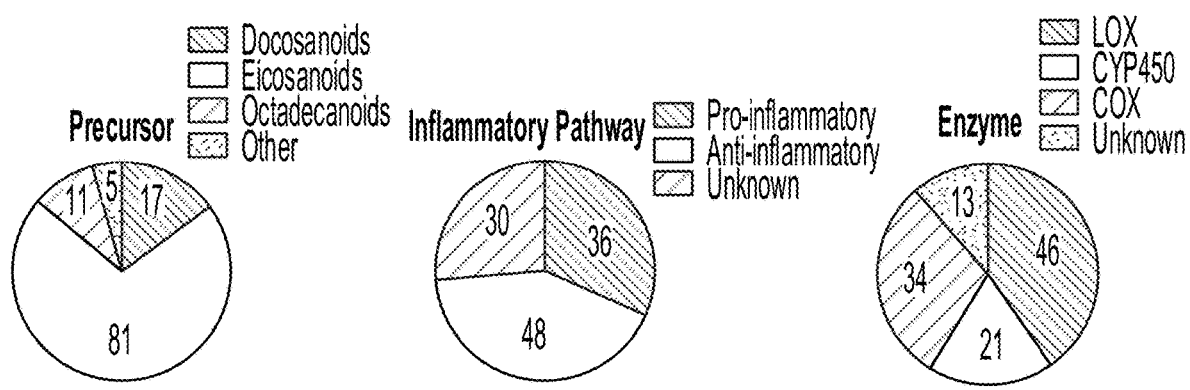
FIGS. 5A-5J depict lipidomic profiles in human subjects after acute exercise and correlations between metabolic markers and VO$_{2peak}$.

Example 1. Identification of 12,13-diHOME as an Exercise-Induced Lipokine in Humans To identify lipokines induced by exercise in humans, two separate cohorts of human subjects were studied to determine if an acute bout of exercise alters the concentration of circulating lipokines. Cohort 1 (n=27) were from the greater Orlando, FL area and were healthy, young and older male subjects with a range of activity levels. Cohort 1 performed 40 min of cycle ergometer exercise at 70% heart rate reserve and blood samples were obtained before, immediately post-, and 3 h post-exercise. Plasma was analyzed by liquid chromatography tandem mass spectrometry (LC-MS/MS) to measure the concentrations of a panel of 88 mediator lipids with annotated signaling properties. These lipids were categorized by several specific attributes including the precursor fatty acids, pro- or anti-inflammatory effects, and on the basis of the enzymes that catalyze the first step in the formation of the lipid (FIG. 5A). Only 1 lipid was significantly increased while 13 lipids were significantly decreased immediately post-exercise (Table 1). The lipid significantly increased in circulation after an acute bout of exercise was the linoleic acid metabolite 12,13-diHOME (FIGS. 1A and 1B). To confirm and extend these findings, we studied a second cohort of subjects from the greater Boston, MA area. Cohort 2 subjects were healthy young (29.4±0.6 year) males (n=6) and females (n=6) that were not engaged in consistent exercise training regimens. Cohort 2 performed 45 min of treadmill running at 75% $VO_{2peak}$ with blood sampling before, 15 min into, immediately post- and 1 h post-exercise. 12,13-diHOME tended to increase 15 min into exercise, was significantly increased immediately post-exercise, and returned to baseline by 1 h post-exercise (FIG. 1C). There were no differences in baseline 12,13-diHOME levels between male and female subjects, although interestingly, exercise increased 12,13-diHOME in all female subjects, while exercise increased 12,13-diHOME in only 4 of 6 male subjects (FIG. 1D).

TABLE 1

Signaling lipids in humans pre- vs. post-exercise
Signaling Lipids in Humans Pre- vs. Post-Exercise

| Lipid | Avg Pre-Exercise | SEM | Avg Post-Exercise | SEM | p-value |
|---|---|---|---|---|---|
| IS-d4-9,10-diHOME | 0.0000 | 0.0000 | 0.0000 | 0.0000 | 0.0000 |
| Tetranor-12-HETE | 0.0473 | 0.0071 | 0.0323 | 0.0035 | 0.0646 |
| 9-oxoODE | 0.1293 | 0.0166 | 0.0790 | 0.0094 | 0.0117 |
| 13-oxoODE | 0.4271 | 0.0442 | 0.2706 | 0.0411 | 0.0122 |
| 9-HOTrE | 0.1101 | 0.0158 | 0.0691 | 0.0110 | 0.0379 |
| 13-HOTrE/13-HOTrE(r) | 0.0531 | 0.0053 | 0.0357 | 0.0042 | 0.0131 |
| 9-HODE | 1.4517 | 0.2541 | 1.3389 | 0.1472 | 0.7026 |
| 13-HODE | 2.0219 | 0.2422 | 1.2251 | 0.1141 | 0.0049 |
| 9(10)-EpOME | 3.8920 | 0.5678 | 2.1015 | 0.2415 | 0.0062 |
| 12(13)-EpOME | 1.4799 | 0.2207 | 1.8134 | 0.1773 | 0.2442 |
| 9,10-diHOME | 1.3140 | 0.2840 | 1.9588 | 0.4610 | 0.2397 |
| 12,13-diHOME* | 1.2308 | 0.1774 | 2.5021 | 0.3343 | 0.0017 |
| 15-deoxy-delta12,14-PGJ2 | 0.0148 | 0.0033 | 0.0126 | 0.0016 | 0.6048 |
| 15-oxoETE | 0.0941 | 0.0146 | 0.0652 | 0.0134 | 0.1494 |
| 18-HEPE | 0.0132 | 0.0021 | 0.0114 | 0.0016 | 0.5482 |
| 15-HEPE | 0.0121 | 0.0023 | 0.0108 | 0.0015 | 0.6982 |
| 12-HEPE | 0.0190 | 0.0030 | 0.0229 | 0.0037 | 0.4653 |
| 5-HEPE | 0.0215 | 0.0036 | 0.0147 | 0.0022 | 0.1483 |
| 11-HEPE | 0.0110 | 0.0019 | 0.0087 | 0.0010 | 0.3565 |
| 8-HEPE | 0.0142 | 0.0036 | 0.0093 | 0.0016 | 0.4145 |
| 9-HEPE | 0.0108 | 0.0008 | 0.0069 | 0.0007 | 0.0030 |
| 12-oxoETE | 0.0132 | 0.0015 | 0.0077 | 0.0013 | 0.0302 |
| 14(15)-EpETE | 0.0089 | 0.0010 | 0.0072 | 0.0008 | 0.3102 |
| 17(18)-EpETE | 0.0078 | 0.0009 | 0.0075 | 0.0012 | 0.9092 |
| 5-oxoETE | 0.0125 | 0.0016 | 0.0113 | 0.0015 | 0.6210 |
| 14(15)-EET | 0.0413 | 0.0050 | 0.0260 | 0.0033 | 0.0140 |
| 11(12)-EET | 0.0061 | 0.0010 | 0.0048 | 0.0005 | 0.3917 |
| 8(9)-EET | 0.0065 | 0.0006 | 0.0053 | 0.0005 | 0.5482 |
| 5(6)-EET | 0.0000 | 0.0000 | 0.0027 | 0.0003 | 0.0000 |
| 15-HETE | 0.0360 | 0.0037 | 0.0310 | 0.0040 | 0.3591 |
| 12-HETE | 0.7583 | 0.2222 | 1.4780 | 0.5768 | 0.2519 |
| 5-HETE | 0.1152 | 0.0133 | 0.1067 | 0.0113 | 0.6270 |
| 20-HETE | 0.0280 | 0.0044 | 0.0230 | 0.0028 | 0.3415 |
| 11-HETE | 0.1799 | 0.0245 | 0.1816 | 0.0347 | 0.9693 |
| 16-HETE | 0.0198 | 0.0048 | 0.0164 | 0.0044 | 0.6330 |
| 17-HETE | 0.0305 | 0.0036 | 0.0292 | 0.0040 | 0.8132 |
| 18-HETE | 0.0463 | 0.0051 | 0.0429 | 0.0054 | 0.6481 |
| 9-HETE | 0.0289 | 0.0069 | 0.0328 | 0.0086 | 0.7265 |
| 8-HETE | 0.0257 | 0.0042 | 0.0241 | 0.0033 | 0.7652 |
| 5-HETrE | 0.0175 | 0.0029 | 0.0151 | 0.0017 | 0.5125 |
| 8-HETrE | 0.0159 | 0.0022 | 0.0197 | 0.0039 | 0.4322 |
| 15-HETrE | 148.2692 | 10.5400 | 130.7339 | 10.0428 | 0.2335 |
| 2,3-dinor-11beta-PGF2a | 0.0060 | 0.0004 | 0.0040 | 0.0003 | 0.0678 |
| tetranor-PGFM | 0.0048 | 0.0004 | 0.0073 | 0.0007 | 0.2945 |
| 12-oxoLTB4 | 0.0108 | 0.0014 | 0.0049 | 0.0004 | 0.0112 |
| PGA2/PGJ2 | 0.0073 | 0.0010 | 0.0056 | 0.0006 | 0.2730 |
| PGB2 | 0.0075 | 0.0010 | 0.0093 | 0.0017 | 0.6495 |
| 15-deoxy-delta12,14-PGD2 | 0.0086 | 0.0010 | 0.0057 | 0.0006 | 0.1730 |

TABLE 1-continued

Signaling lipids in humans pre- vs. post-exercise
Signaling Lipids in Humans Pre- vs. Post-Exercise

| Lipid | Avg Pre-Exercise | SEM | Avg Post-Exercise | SEM | p-value |
|---|---|---|---|---|---|
| 13,14-dihydro-15-keto PGA2 | 0.0100 | 0.0018 | 0.0128 | 0.0031 | 0.5429 |
| Bicyclo PGE2 | 0.0075 | 0.0011 | 0.0058 | 0.0007 | 0.2913 |
| delta12-PGJ2 | 0.0072 | 0.0010 | 0.0066 | 0.0010 | 0.7760 |
| LTB4 | 0.0158 | 0.0033 | 0.0165 | 0.0023 | 0.8642 |
| 5,6-diHETE | 0.0183 | 0.0043 | 0.0366 | 0.0113 | 0.1480 |
| 5,15-diHETE | 0.0048 | 0.0006 | 0.0062 | 0.0007 | 0.3230 |
| Hepoxilin A3 | 0.0100 | 0.0014 | 0.0087 | 0.0007 | 0.4798 |
| 14,15-diHETE | 0.0102 | 0.0013 | 0.0068 | 0.0011 | 0.1785 |
| 17,18-diHETE | 0.1301 | 0.0206 | 0.1379 | 0.0129 | 0.7505 |
| PGA1 | 0.0067 | 0.0005 | 0.0068 | 0.0011 | 0.9256 |
| 5,6-diHETrE | 0.0147 | 0.0031 | 0.0177 | 0.0021 | 0.4621 |
| 8,9-diHETrE | 0.0306 | 0.0043 | 0.0280 | 0.0044 | 0.6653 |
| 11,12-diHETrE | 0.1568 | 0.0159 | 0.1290 | 0.0106 | 0.1526 |
| 14,15-diHETrE | 0.1561 | 0.0193 | 0.1517 | 0.0106 | 0.8433 |
| 2,3-dinor TxB2 | 0.0062 | 0.0006 | 0.0065 | 0.0006 | 0.7845 |
| 17-HDHA | 0.8257 | 0.7073 | 0.2912 | 0.2441 | 0.5392 |
| 14-HDHA | 0.0065 | 0.0011 | 0.0120 | 0.0019 | 0.0516 |
| 7-HDHA | 0.0064 | 0.0011 | 0.0060 | 0.0009 | 0.8200 |
| 4-HDHA | 0.0153 | 0.0026 | 0.0100 | 0.0020 | 0.1535 |
| 8-HDHA | 0.0116 | 0.0015 | 0.0062 | 0.0006 | 0.0357 |
| 10-HDHA | 0.0147 | 0.0024 | 0.0114 | 0.0015 | 0.3046 |
| 11-HDHA | 0.0119 | 0.0014 | 0.0115 | 0.0016 | 0.8833 |
| 13-HDHA | 0.0113 | 0.0021 | 0.0062 | 0.0008 | 0.1057 |
| 16-HDHA | 0.0113 | 0.0021 | 0.0102 | 0.0014 | 0.6820 |
| 20-HDHA | 0.0106 | 0.0016 | 0.0101 | 0.0020 | 0.8686 |
| 19(20)-EpDPE | 0.0168 | 0.0021 | 0.0096 | 0.0017 | 0.0180 |
| 16(17)-EpDPE | 0.0120 | 0.0015 | 0.0122 | 0.0021 | 0.9410 |
| PGD3/PGE3 | 0.0083 | 0.0011 | 0.0070 | 0.0010 | 0.5712 |
| 15-keto-PGE2 | 0.0000 | 0.0000 | 0.0084 | 0.0000 | 0.0000 |
| PGK2 | 0.0060 | 0.0010 | 0.0065 | 0.0010 | 0.8381 |
| 13,14-dihydro-15-keto PGE2 | 0.0075 | 0.0012 | 0.0093 | 0.0009 | 0.3801 |
| 13,14-dihydra-15-keto PGD2 | 0.0072 | 0.0012 | 0.0060 | 0.0006 | 0.5040 |
| 15-keto-PGF2a | 0.0076 | 0.0013 | 0.0057 | 0.0006 | 0.4163 |
| PGE2/PGD2 | 0.0105 | 0.0016 | 0.0140 | 0.0020 | 0.2343 |
| PGD2 | 0.0083 | 0.0012 | 0.0063 | 0.0005 | 0.2691 |
| LXA4 | 0.0082 | 0.0014 | 0.0063 | 0.0010 | 0.3910 |
| LXB4 | 0.0062 | 0.0011 | 0.0073 | 0.0011 | 0.6203 |
| PGF2a | 0.0095 | 0.0013 | 0.0126 | 0.0017 | 0.2042 |
| 8-iso PGF2a | 0.0099 | 0.0013 | 0.0117 | 0.0015 | 0.4320 |
| 5-iPF2a-VI | 0.0241 | 0.0094 | 0.0149 | 0.0016 | 0.3548 |
| PGE1/PGD1 | 0.0076 | 0.0009 | 0.0075 | 0.0008 | 0.9684 |
| 11-beta-PGF2a/PGF2b | 0.0101 | 0.0013 | 0.0114 | 0.0015 | 0.5718 |
| 13,14-dihydro-15-keto PGF2a | 0.0106 | 0.0011 | 0.0124 | 0.0017 | 0.4132 |
| Maresin1 | 0.0000 | 0.0000 | 0.0036 | 0.0003 | 0.0000 |
| PD1 | 0.0086 | 0.0011 | 0.0074 | 0.0013 | 0.6604 |
| 19,20-diHDPA | 0.0845 | 0.0130 | 0.0843 | 0.0084 | 0.9927 |
| 20-carboxy LTB4 | 0.0319 | 0.0085 | 0.0133 | 0.0023 | 0.1036 |
| TxB3 | 0.0088 | 0.0011 | 0.0146 | 0.0037 | 0.2241 |
| 11-dehydro TxB2 | 0.0069 | 0.0014 | 0.0052 | 0.0006 | 0.4553 |
| 19/20-OH PGE2 | 0.0065 | 0.0006 | 0.0059 | 0.0004 | 0.7715 |
| 6-keto PGE1 | 0.0043 | 0.0005 | 0.0059 | 0.0006 | 0.2995 |
| TxB2 | 1.9404 | 0.7048 | 3.0967 | 1.4077 | 0.4668 |
| 6-keto-PGF1a | 0.0171 | 0.0032 | 0.0208 | 0.0058 | 0.6258 |
| 19/20-OH PGF2a | 0.0079 | 0.0009 | 0.0059 | 0.0005 | 0.2707 |
| 6,15-diketo-13,14-dihydro PGF1a | 0.0077 | 0.0010 | 0.0057 | 0.0004 | 0.2658 |
| RvD1 | 0.0064 | 0.0006 | 0.0043 | 0.0004 | 0.1566 |
| RvD2 | 0.0061 | 0.0011 | 0.0080 | 0.0017 | 0.6787 |
| LTE4 | 0.0127 | 0.0018 | 0.0009 | 0.0000 | 0.0000 |
| LTD4 | 0.0060 | 0.0013 | 0.0062 | 0.0007 | 0.9620 |
| LTC4 | 0.0082 | 0.0001 | 0.0048 | 0.0004 | 0.0429 |
| d4-9-HODE | 0.0000 | 0.0000 | 0.0000 | 0.0000 | 0.0000 |
| d8-5S-HETE | 0.0000 | 0.0000 | 0.0000 | 0.0000 | 0.0000 |
| d4-LTB4 | 0.0000 | 0.0000 | 0.0000 | 0.0000 | 0.0000 |
| d4-PGE2 | 0.0000 | 0.0000 | 0.0000 | 0.0000 | 0.0000 |
| PGF1a | 0.0943 | 0.0082 | 0.0943 | 0.0079 | 0.9993 |
| 13,14-dihydro PGE1 | 0.0422 | 0.0066 | 0.0348 | 0.0047 | 0.4164 |
| PGE2/PGD2 | 0.0105 | 0.0016 | 0.0140 | 0.0020 | 0.2343 |
| PGD2 | 0.0083 | 0.0012 | 0.0063 | 0.0005 | 0.2691 |
| LXA4 | 0.0082 | 0.0014 | 0.0063 | 0.0010 | 0.3910 |
| LXB4 | 0.0062 | 0.0011 | 0.0073 | 0.0011 | 0.6203 |
| PGF2a | 0.0095 | 0.0013 | 0.0126 | 0.0017 | 0.2042 |
| 8-iso PGF2a | 0.0099 | 0.0013 | 0.0117 | 0.0015 | 0.4320 |
| 5-iPF2a-VI | 0.0241 | 0.0094 | 0.0149 | 0.0016 | 0.3548 |
| PGE1/PGD1 | 0.0076 | 0.0009 | 0.0075 | 0.0008 | 0.9684 |
| 11-beta-PGF2a/PGF2b | 0.0101 | 0.0013 | 0.0114 | 0.0015 | 0.5718 |

TABLE 1-continued

Signaling lipids in humans pre- vs. post-exercise
Signaling Lipids in Humans Pre- vs. Post-Exercise

| Lipid | Avg Pre-Exercise | SEM | Avg Post-Exercise | SEM | p-value |
|---|---|---|---|---|---|
| 13,14-dihydro-15-keto PGF2a | 0.0106 | 0.0011 | 0.0124 | 0.0017 | 0.4132 |
| Maresin1 | 0.0000 | 0.0000 | 0.0036 | 0.0003 | 0.0000 |
| PD1 | 0.0086 | 0.0011 | 0.0074 | 0.0013 | 0.6604 |
| 19,20-diHDPA | 0.0845 | 0.0130 | 0.0843 | 0.0084 | 0.9927 |
| 20-carboxy LTB4 | 0.0319 | 0.0085 | 0.0133 | 0.0023 | 0.1036 |
| TxB3 | 0.0088 | 0.0011 | 0.0146 | 0.0037 | 0.2241 |
| 11-dehydro TxB2 | 0.0069 | 0.0014 | 0.0052 | 0.0006 | 0.4553 |
| 19/20-OH PGE2 | 0.0065 | 0.0006 | 0.0059 | 0.0004 | 0.7715 |
| 6-keto PGE1 | 0.0043 | 0.0005 | 0.0059 | 0.0006 | 0.2995 |
| TxB2 | 1.9404 | 0.7048 | 3.0967 | 1.4077 | 0.4668 |
| 6-keto-PGF1a | 0.0171 | 0.0032 | 0.0208 | 0.0058 | 0.6258 |
| 19/20-OH PGF2a | 0.0079 | 0.0009 | 0.0059 | 0.0005 | 0.2707 |
| 6,15-diketo-13,14-dihydro PGF1a | 0.0077 | 0.0010 | 0.0057 | 0.0004 | 0.2658 |
| RvD1 | 0.0064 | 0.0006 | 0.0043 | 0.0004 | 0.1566 |
| RvD2 | 0.0061 | 0.0011 | 0.0080 | 0.0017 | 0.6787 |
| LTE4 | 0.0127 | 0.0018 | 0.0009 | 0.0000 | 0.0000 |
| LTD4 | 0.0060 | 0.0013 | 0.0062 | 0.0007 | 0.9620 |
| LTC4 | 0.0082 | 0.0001 | 0.0048 | 0.0004 | 0.0429 |
| d4-9-HODE | 0.0000 | 0.0000 | 0.0000 | 0.0000 | 0.0000 |
| d8-5S-HETE | 0.0000 | 0.0000 | 0.0000 | 0.0000 | 0.0000 |
| d4-LTB4 | 0.0000 | 0.0000 | 0.0000 | 0.0000 | 0.0000 |
| d4-PGE2 | 0.0000 | 0.0000 | 0.0000 | 0.0000 | 0.0000 |
| PGF1a | 0.0943 | 0.0082 | 0.0943 | 0.0079 | 0.9993 |
| 13,14-dihydro PGE1 | 0.0422 | 0.0066 | 0.0348 | 0.0047 | 0.4164 |

Figure 1E:
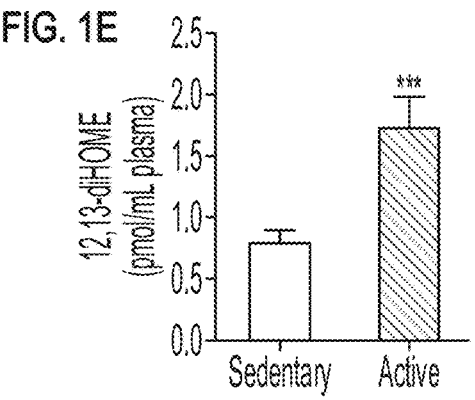
Figure 1F:
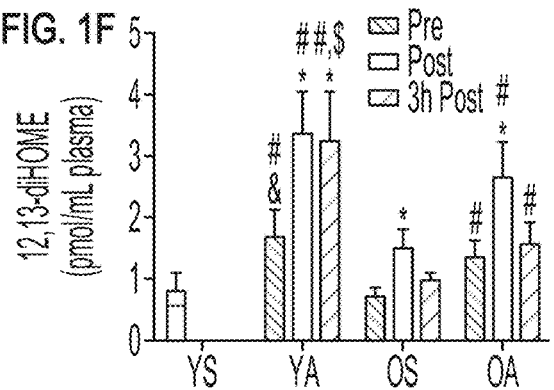

Example 2. Identification of the Effects of Activity Level on Exercise-Stimulated 12,13-diHOME To determine if chronic levels of physical activity affect baseline concentrations of 12,13-diHOME, an analysis of sedentary (n=30) and active (n=13) subjects from Cohorts 1 and 2 was performed. The data indicated that active subjects had significantly higher 12,13-diHOME concentrations at baseline (FIG. 1E), indicating that activity status could be a factor in determining 12,13-diHOME concentrations. Because Cohort 1 had male subjects with a range of ages and activity levels, an analysis of the effects of exercise on 12,13-diHOME levels based on both factors was performed. These male subjects were categorized as: young sedentary (YS) (age 24-42 year; n=4); young active (age 24-40 year; n=6); older sedentary (age 65-90 year; n=14); and older active (age 65-90 year; n=7). Historical data from a recent study was used provide a comparison to the cohort of young sedentary (YS) male subjects (age 24-42 year; n=4) (Lynes et al., 2017). Active subjects performed aerobic exercise at least 3 days/week during the previous 6 months, and sedentary performed <1 exercise session per week. Young active (YA), older active (OA), and older sedentary (OS) subjects all demonstrated a significant increase in 12,13-diHOME immediately post-exercise, although the effect was greater in the active subjects (FIG. 1F). At 3 h post-exercise, only YA subjects demonstrated an increase in circulating 12,13-diHOME. Taken together, these data show that a single bout of exercise increases circulating 12,13-diHOME in humans regardless of gender, age, or activity level.

Figure 1G:
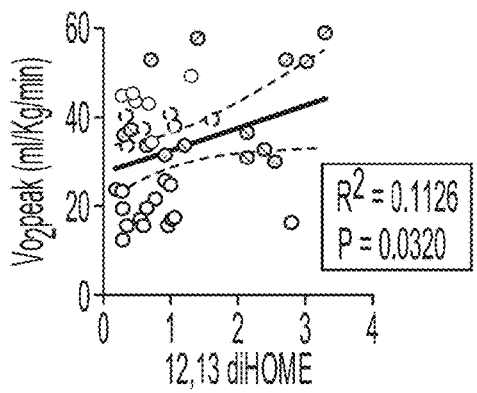
Figure 1H:
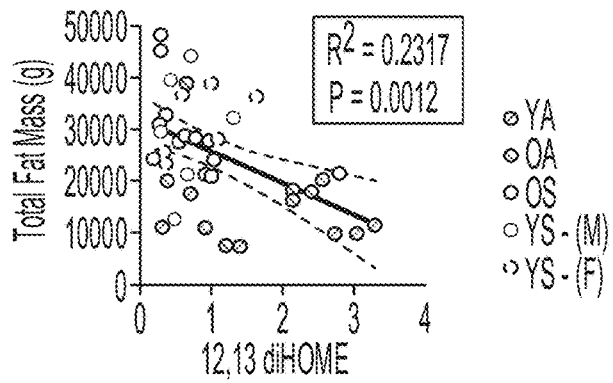
Figure 1I:
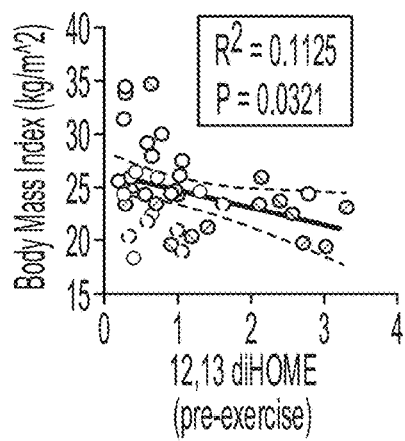
Figure 5B:
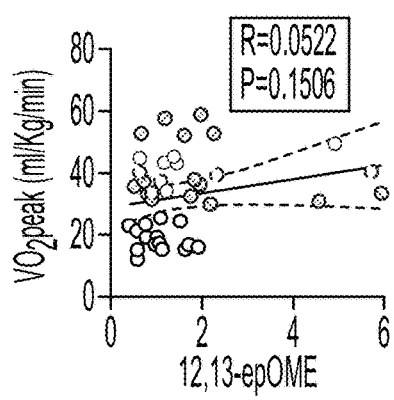
Figure 5C:
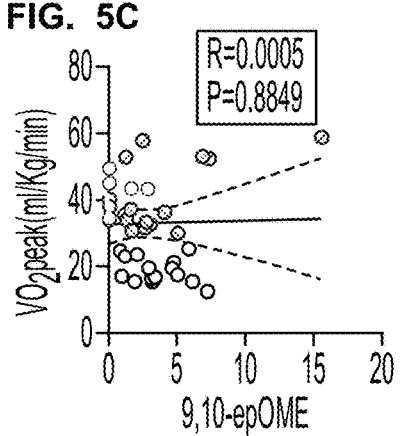
Figure 5D:
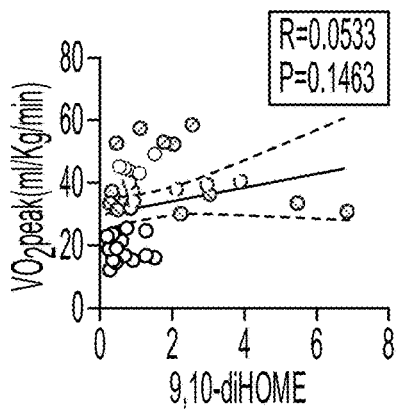
Figure 5E:
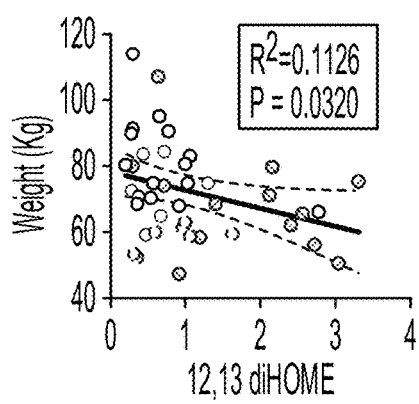
Figure 5F:
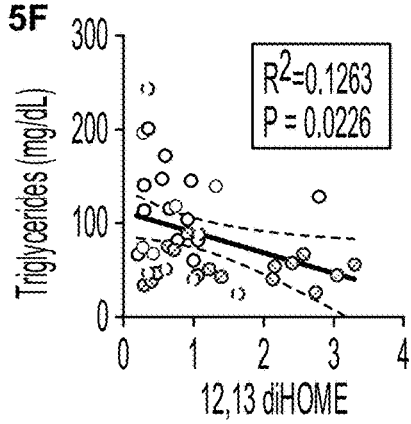
Figure 5G:
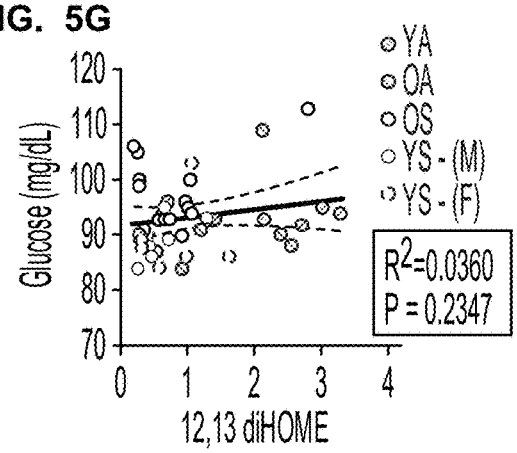
Figure 5H:
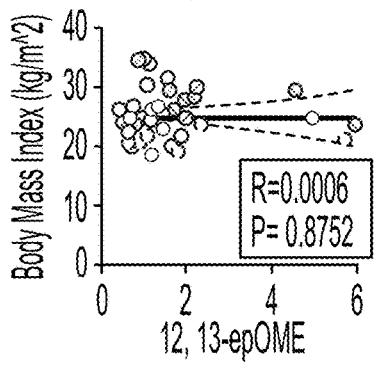
Figure 5I:
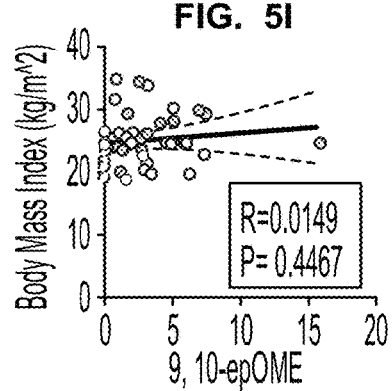
Figure 5J:
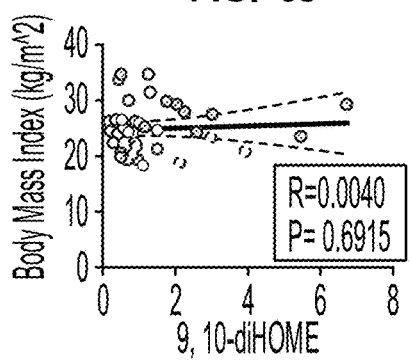

Example 3. Determination of Whether Resting 12,13-diHOME Concentrations are Correlated with Fat Mass To determine if a relationship exists between 12,13-diHOME levels and cardiorespiratory fitness, assays were performed to measure $VO_{2peak}$. The data demonstrated that 12,13-diHOME was positively correlated with $VO_{2peak}$ in both cohorts (FIG. 1G). The direct correlation between cardiovascular fitness and 12,13-diHOME was specific for 12,13-diHOME. Therefore, $VO_{2peak}$ was not significantly correlated with other linoleic acid metabolites including 12,13-epOME, 9,10-epOME, and 9,10-diHOME (FIGS. 5B-5D). The data also demonstrated that 12,13-diHOME also correlated with total fat mass (FIG. 1H), body mass index (BMI) (FIG. 1I), body weight (FIG. 5E), and triglycerides (FIG. 5F). There was no correlation between 12,13-diHOME and fasting glucose concentrations (FIG. 5G), and none of these factors were correlated with 12,13-epOME, 9,10-epOME, and 9,10-diHOME (FIGS. 5H-5J; data not shown).

Since 12,13-diHOME was positively correlated with $VO_{2peak}$, and negatively correlated with fat mass and BMI, co-variate analyses were performed to determine whether the increase in 12,13-diHOME was driven primarily by fat mass. Co-variate analyses revealed that when % fat mass is accounted for, 12,13-diHOME is only significantly correlated with circulating triglycerides (Table 2).

TABLE 2

Spearman and Pearson correlation coefficient with % fat mass as a covariate
% Fat Mass as a Covariate

| Variable correlated with 12,13 diHOME | R | P |
|---|---|---|
| Spearman correlation coefficient | | |
| $VO_{2peak}$ (ml/kg/min) | 0.1214 | 0.4679 |
| Body Mass Index (kg/m$^2$) | −0.2877 | 0.0647 |
| Triglycerides (mg/dL) | −0.3554 | 0.0209 |
| Weight Average (kg) | −0.2433 | 0.1410 |
| Pearson correlation coefficient | | |
| VO2peak (ml/Kg/min) | 0.1889 | 0.2560 |
| Body Mass Index (kg/m'2) | −0.2968 | 0.0563 |
| Triglycerides (mg/dL) | −0.3827 | 0.0124 |
| Weight Average (kg) | −0.2403 | 0.1462 |

Figure 1J:
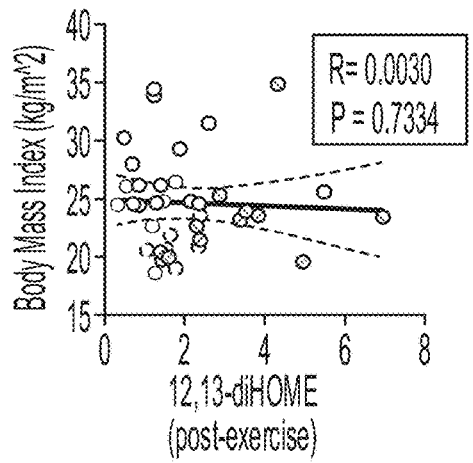
Figure 1K:
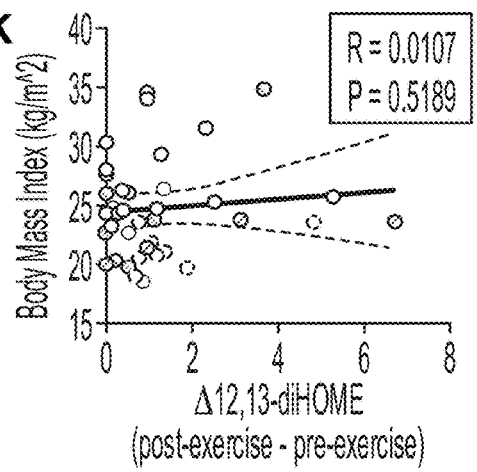

Given the relationship between BMI and baseline 12,13-diHOME concentrations, assays were performed to determine if BMI or fat mass were important factors in the increase in 12,13-diHOME in response to exercise. The data demonstrated that there was no correlation between BMI and Immediate Post-Exercise 12,13-diHOME concentrations (FIG. 1J) or between BMI and the increase (delta) in 12,13-diHOME with acute exercise (FIG. 1K). Thus, the post-exercise increase in 12,13-diHOME is independent of BMI and indicated a specific effect of acute exercise to increase 12,13-diHOME.

Figure 2A:
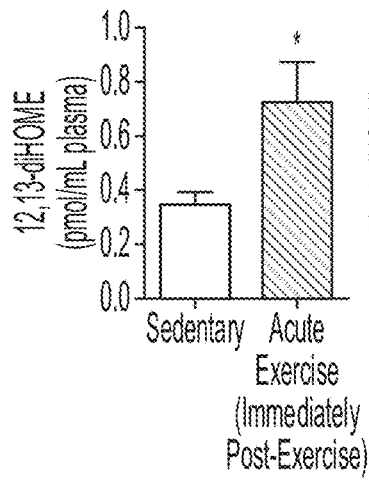
FIGS. 2A-2K depict an increase in 12,13-diHOME in mice following exercise and depict brown adipose tissue (BAT) is required for exercise-induced increases in 12,13-diHOME.
Figure 2B:
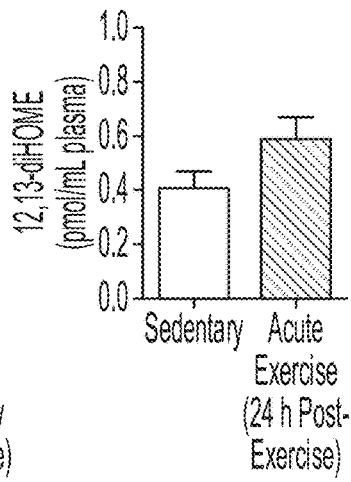
Figure 2C:
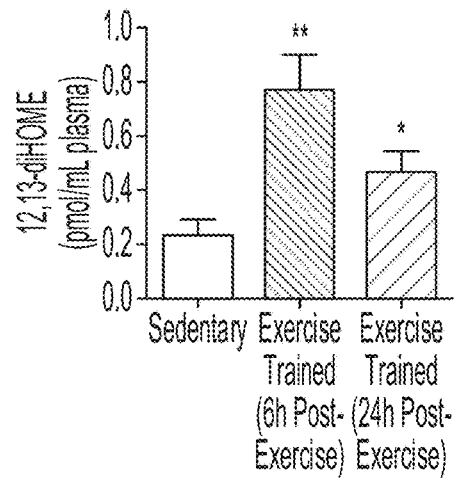

Example 4. Determination of Whether 12,13-diHOME is Increased with Exercise in Mice A mouse model was used to investigate mechanisms of exercise regulation of 12,13-diHOME. Interestingly, 12,13-diHOME concentrations were lower in mice compared to humans, which may be due to differences in fatty acid precursors, enzyme activity, or general animal physiology. To study exercise in mice, 10 week old C57BL/6 male mice were either: housed singularly in static cages for 3 weeks (Sedentary); housed singularly in static cages for 3 weeks followed by a single bout of moderate intensity treadmill exercise (Acute Exercise); or housed singularly in a cage containing an exercise wheel for 3 weeks (Exercise Trained; 7.4±0.6 km/day). Consistent with the human studies, a single bout of exercise significantly increased circulating 12,13-diHOME in mice (FIG. 2A). At 24 h post-exercise, there was no longer a significant increase in 12,13-diHOME (FIG. 2B). Chronic exercise training by wheel running also significantly increased circulating 12,13-diHOME at both 6 and 24 h after removal of mice from wheel cages (FIG. 2C). Body mass and fat mass were shown to decrease after 3 weeks of wheel running (FIG. 6A) and thus, similar to the human data, it is likely that a decrease in fat mass contributes to the increase in 12,13-diHOME in the trained mice.

Figure 2D:
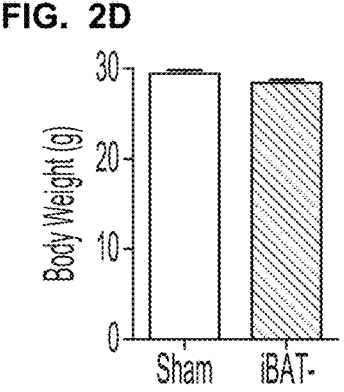
Figure 2E:
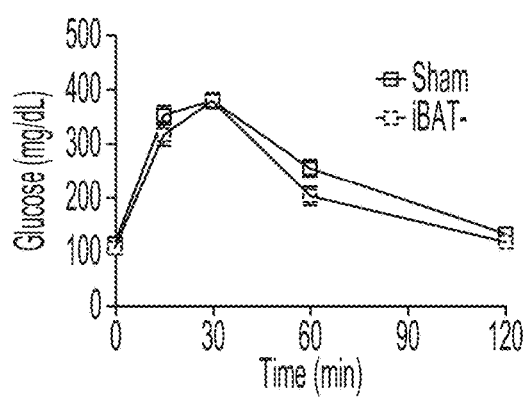
Figure 2F:
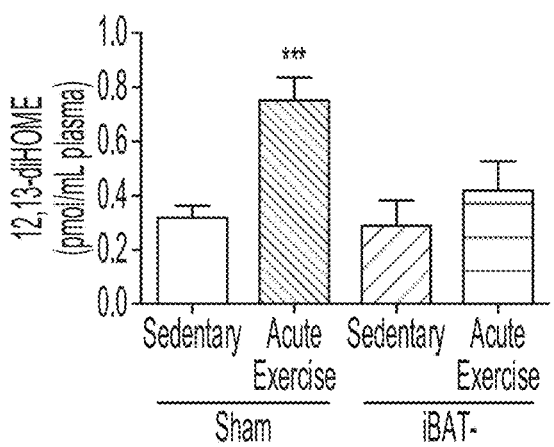

Example 5. Analysis to Determine Whether BAT is the Tissue Source for the Exercise-Induced Increase in Circulating 12,13-diHOME To investigate whether brown adipose tissue (BAT) was the tissue source of the exercise-induced increase in 12,13-diHOME, mice underwent sham surgery or had BAT surgically removed from the intracapsular region (iBAT-), the depot which accounts for ~60% of BAT in a mouse. Eight weeks later, body weights and glucose tolerance were shown to not be different between Sham and iBAT-mice (FIGS. 2D and 2E). There was no difference in basal 12,13-diHOME concentrations between Sham and iBAT-mice, indicating that there are other tissues that contribute to circulating 12,13-diHOME levels (FIG. 2F). Exercise significantly increased 12,13-diHOME in the Sham mice, but the effects of exercise were fully blunted in the iBAT-mice (FIG. 2F). Thus, although liver, kidney, and white adipose tissue have all been shown to express 12,13-diHOME, this assay identified iBAT as the tissue responsible for the exercise-induced increase in circulating 12,13-diHOME.

Figure 2G:
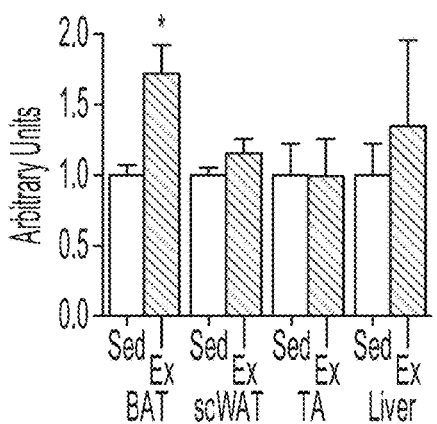
Figure 2H:
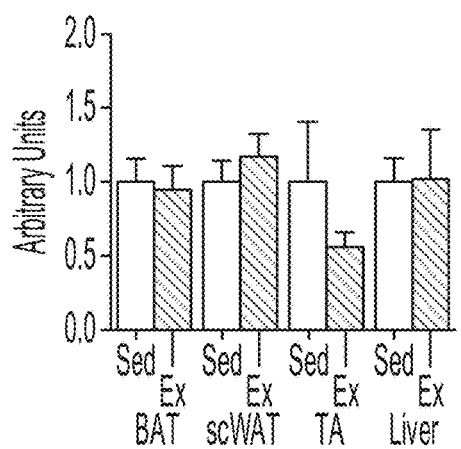

The effects of exercise training on the expression of genes responsible for the production of 12,13-diHOME was subsequently analyzed. The biosynthesis of 12,13-diHOME is regulated by soluble epoxide hydrolases (sEH) of which Ephx1 and Ephx2 are the major isoforms expressed in adipose tissue (Lynes et al., 2017). A single bout of exercise increased Ephx1 expression in BAT, but did not affect Ephx1 expression in subcutaneous white adipose tissue (scWAT), tibialis anterior muscle (TA), or liver (FIG. 2G). Data also demonstrated that Ephx2 was not changed in any tissue after exercise (FIG. 2H).

Figure 2I:
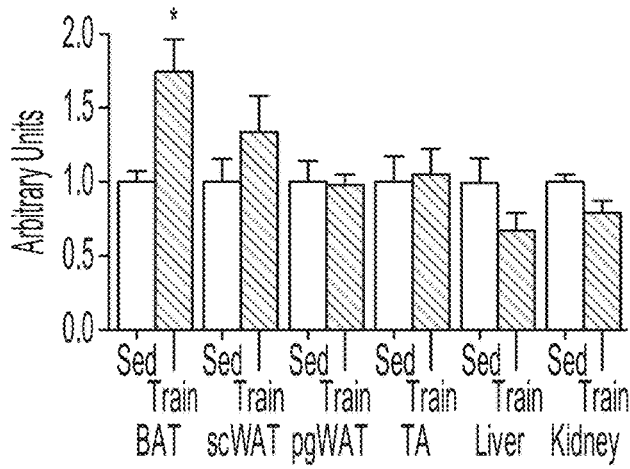
Figure 2J:
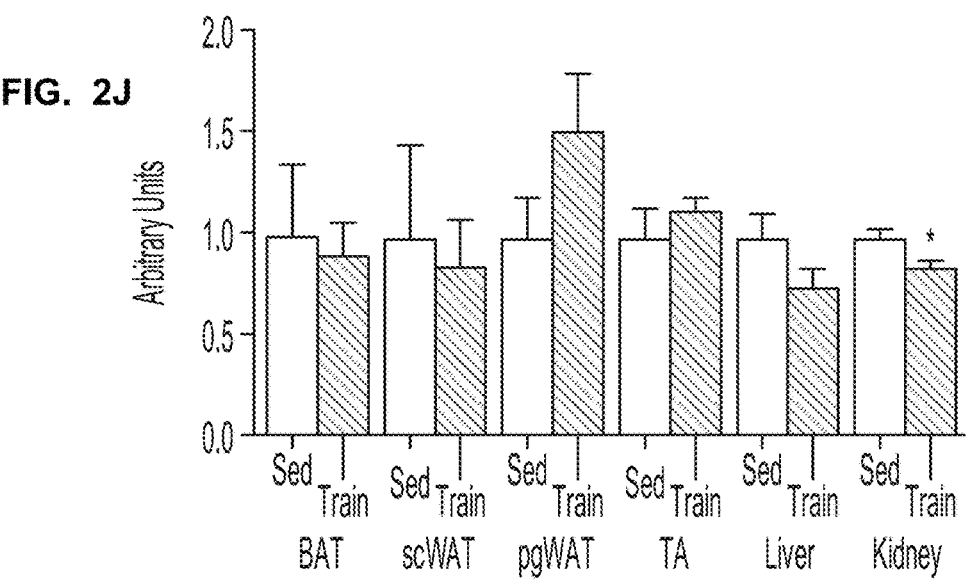

After 3 weeks of exercise training, gene expression of Ephx1 and Ephx2 was measured in BAT, scWAT, perigonadal white adipose tissue (pgWAT), tibialis anterior muscle, liver, and kidney. The data demonstrated that training increased Ephx1 expression in BAT (FIG. 2I), but not in any other tissue. Exercise training had no effect on Ephx2 expression in BAT, scWAT, pgWAT, muscle, or liver, but significantly decreased Ephx2 expression in the kidney (FIG. 2J). The function of the decrease in Ephx2 in the kidney with exercise is unknown. These data indicated that both a single bout of exercise and exercise training increased Ephx1 expression only in BAT.

Figure 2K:
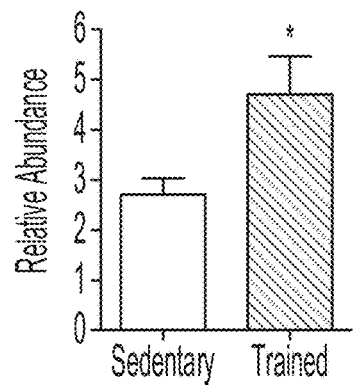

To determine whether exercise training increased 12,13-diHOME in BAT, mice underwent 3 weeks of exercise training by wheel running after which BAT was analyzed by LC-MS/MS lipidomics. Of the 88 lipid species measured (Table 3), only 12,13-diHOME was significantly increased in BAT from exercise-trained mice (FIG. 2K). Taken together, these data indicated that BAT is the tissue source for the exercise-induced increase in circulating 12,13-diHOME.

TABLE 3

Signaling lipids in mouse BAT, sedentary vs. trained
Signaling Lipids in BAT (Sedentary vs. Trained)

| Lipid | Avg Sed | SEM | Avg Train | SEM | p-value |
|---|---|---|---|---|---|
| 9-oxoODE | 2.710 | 0.623 | 2.828 | 0.728 | 0.904 |
| 13-oxoODE | 1.629 | 0.282 | 2.739 | 0.885 | 0.277 |
| 9-HOTrE | 0.364 | 0.089 | 0.496 | 0.167 | 0.505 |
| HOTrE/13-HOTrE | 0.269 | 0.059 | 0.375 | 0.086 | 0.338 |
| 9-HODE | 13.241 | 2.444 | 17.024 | 5.984 | 0.578 |
| 13-HODE | 20.447 | 3.203 | 23.406 | 8.180 | 0.747 |
| 9(10)-EpOME | 13.643 | 1.763 | 17.130 | 3.027 | 0.349 |
| 12(13)-EpOME | 10.681 | 1.586 | 12.628 | 2.859 | 0.568 |
| 9,10-diHOME | 3.471 | 0.381 | 5.366 | 1.055 | 0.140 |
| 12,13-diHOME* | 2.704 | 0.317 | 4.703 | 0.738 | 0.0427 |
| 18-HEPE | 0.143 | 0.021 | 0.170 | 0.029 | 0.467 |
| 15-HEPE | 0.093 | 0.010 | 0.115 | 0.027 | 0.481 |
| 12-HEPE | 1.637 | 0.238 | 1.798 | 0.655 | 0.825 |
| 5-HEPE | 0.189 | 0.026 | 0.241 | 0.048 | 0.368 |
| 11-HEPE | 0.107 | 0.013 | 0.140 | 0.027 | 0.316 |
| 8-HEPE | 0.062 | 0.008 | 0.083 | 0.024 | 0.422 |
| 15-oxoETE | 0.059 | 0.016 | 0.055 | 0.010 | 0.847 |
| 9-HEPE | 0.038 | 0.007 | 0.054 | 0.019 | 0.457 |
| 14(15)-EET | 0.274 | 0.054 | 0.286 | 0.051 | 0.873 |
| 11(12)-EET | 0.415 | 0.069 | 0.489 | 0.127 | 0.626 |
| 8(9)-EET | 0.057 | 0.028 | 0.071 | 0.033 | 0.758 |
| 5(6)-EET | 0.100 | 0.014 | 0.102 | 0.026 | 0.941 |
| 15-HETE | 0.406 | 0.056 | 0.468 | 0.110 | 0.632 |
| 12-HETE | 3.721 | 1.100 | 2.277 | 0.772 | 0.311 |
| 5-HETE | 0.629 | 0.111 | 0.569 | 0.091 | 0.682 |
| 20-HETE | 0.007 | 0.003 | 0.011 | 0.004 | 0.476 |
| 11-HETE | 0.889 | 0.110 | 0.947 | 0.188 | 0.797 |
| 16-HETE | 0.007 | 0.007 | 0.021 | 0.013 | 0.332 |
| 17-HETE | 0.014 | 0.004 | 0.024 | 0.008 | 0.273 |
| 18-HETE | 0.091 | 0.008 | 0.123 | 0.028 | 0.311 |
| 9-HETE | 0.216 | 0.044 | 0.151 | 0.038 | 0.291 |
| 8-HETE | 0.256 | 0.040 | 0.246 | 0.062 | 0.892 |
| all trans-LTB4 | 0.013 | 0.007 | 0.003 | 0.002 | 0.235 |
| LTB4 | 0.018 | 0.006 | 0.006 | 0.003 | 0.096 |
| 5,6-diHETE | 0.018 | 0.008 | 0.021 | 0.010 | 0.802 |
| 5,15-diHETE | 0.001 | 0.001 | 0.001 | 0.000 | 0.973 |
| Hepoxllin A3 | 0.029 | 0.013 | 0.038 | 0.015 | 0.686 |
| 17-HDHA | 0.078 | 0.009 | 0.113 | 0.030 | 0.317 |
| 14-HDHA | 0.431 | 0.086 | 0.477 | 0.132 | 0.777 |
| 7-HDHA | 0.055 | 0.010 | 0.052 | 0.009 | 0.775 |
| 4-HDHA | 0.200 | 0.030 | 0.268 | 0.048 | 0.264 |
| 8-HDHA # | 0.101 | 0.039 | 0.000 | 0.000 | 0.049 |
| 10-HDHA | 0.282 | 0.080 | 0.324 | 0.049 | 0.664 |
| 11-HDHA | 0.122 | 0.014 | 0.131 | 0.026 | 0.778 |

TABLE 3-continued

Signaling lipids in mouse BAT, sedentary vs. trained
Signaling Lipids in BAT (Sedentary vs. Trained)

| Lipid | Avg Sed | SEM | Avg Train | SEM | p-value |
|---|---|---|---|---|---|
| 13-HDHA | 0.242 | 0.038 | 0.292 | 0.064 | 0.525 |
| 16-HDHA | 0.281 | 0.037 | 0.321 | 0.050 | 0.537 |
| 20-HDHA | 0.237 | 0.043 | 0.283 | 0.058 | 0.539 |
| 19(20)-EpDPE | 0.054 | 0.034 | 0.025 | 0.016 | 0.467 |
| 16(17)-EpDPE | 0.168 | 0.030 | 0.147 | 0.042 | 0.692 |
| PGE2/PGD2 | 0.089 | 0.026 | 0.056 | 0.013 | 0.302 |
| PGD2 | 0.038 | 0.005 | 0.025 | 0.005 | 0.084 |
| LXA4 | 0.028 | 0.011 | 0.033 | 0.006 | 0.726 |
| LXB4 | 0.006 | 0.003 | 0.005 | 0.002 | 0.942 |
| 15-keto-PGF2a | 0.007 | 0.002 | 0.006 | 0.002 | 0.794 |
| dihydro-15-keto | 0.028 | 0.011 | 0.014 | 0.006 | 0.314 |
| dihydro-15-keto | 0.020 | 0.005 | 0.027 | 0.008 | 0.493 |
| PGF2a | 0.031 | 0.009 | 0.018 | 0.002 | 0.217 |
| PGE1/D1 | 0.017 | 0.005 | 0.021 | 0.006 | 0.637 |
| 8-iso PGF2a | 0.030 | 0.009 | 0.020 | 0.003 | 0.336 |
| 5-iPF2a-VI | 0.008 | 0.003 | 0.004 | 0.001 | 0.302 |
| PD1 | 0.061 | 0.042 | 0.023 | 0.008 | 0.410 |
| TxB2 | 0.029 | 0.008 | 0.017 | 0.006 | 0.224 |
| 6-keto-PGF1a | 0.018 | 0.012 | 0.003 | 0.002 | 0.245 |
| 19/20-OH PGF2a | 0.002 | 0.001 | 0.002 | 0.001 | 0.915 |
| RvD1 | 0.003 | 0.001 | 0.005 | 0.002 | 0.565 |
| RvD2 | 0.002 | 0.001 | 0.002 | 0.001 | 0.940 |
| LTE4 | 0.000 | 0.000 | 0.000 | 0.000 | N/A |
| LTD4 | 0.002 | 0.001 | 0.001 | 0.000 | 0.504 |
| LTC4 | 0.001 | 0.000 | 0.000 | 0.000 | 0.094 |
| PGF1a | 0.000 | 0.000 | 0.001 | 0.001 | 0.363 |
| PGD3 | 0.010 | 0.004 | 0.006 | 0.002 | 0.494 |
| PGA2/PGJ2 | 0.012 | 0.008 | 0.003 | 0.001 | 0.293 |
| PGB2 | 0.003 | 0.002 | 0.001 | 0.001 | 0.545 |
| eoxy-delta12,14-P | 0.007 | 0.002 | 0.007 | 0.003 | 0.977 |
| 5,6-DiHETrE # | 0.031 | 0.007 | 0.013 | 0.003 | 0.050 |
| 8,9-DiHETrE # | 0.067 | 0.010 | 0.025 | 0.004 | 0.008 |
| 11,12-DiHETrE | 0.101 | 0.021 | 0.070 | 0.017 | 0.268 |
| 14,15-DiHETrE | 0.174 | 0.031 | 0.118 | 0.016 | 0.144 |
| 5-HETrE | 0.019 | 0.005 | 0.036 | 0.015 | 0.341 |
| 8-HETrE | 0.172 | 0.020 | 0.137 | 0.032 | 0.374 |
| 15-HETrE | 0.485 | 0.045 | 0.491 | 0.088 | 0.957 |
| 19,20-DiHDPA | 0.210 | 0.027 | 0.238 | 0.040 | 0.577 |
| dinor-11beta-PG | 0.001 | 0.001 | 0.001 | 0.000 | 0.746 |
| eoxy-delta12,14 | 0.011 | 0.005 | 0.009 | 0.004 | 0.868 |
| TxB3 | 0.004 | 0.002 | 0.004 | 0.001 | 0.843 |
| Tetranor-12-HETE | 0.008 | 0.002 | 0.006 | 0.002 | 0.560 |

Example 6. Analysis to Determine Whether 12,13-diHOME Increases Skeletal Muscle Fatty Acid Uptake In Vivo A major source of energy for the working skeletal muscles during exercise comes from the uptake and oxidation of fatty acids. To determine whether 12,13-diHOME increases fatty acid uptake and oxidation in skeletal muscle in vivo, a mouse model, ACTA1Cre+/−Rosa(stop)Luc+/−mice, was generated that constitutively expressed a bioluminescent reporter in skeletal muscle. Mice were injected intravenously with FFA-SS-Luc, which is a fatty acid conjugated to luciferin (Henkin et al., 2012; Liao et al., 2005), in the presence of 12,13-diHOME or a vehicle control. Injection of 12,13-diHOME increased fatty acid uptake in skeletal muscle (FIGS. 3A and 3B). This increase was most prominent immediately after injection and remained significantly elevated above vehicle for 10 min. These surprising in vivo data provided a potential physiological function for the exercise-induced increases in 12,13-diHOME. Consistent with these data, acute injection of wild-type mice with 12,13-diHOME resulted in a decreased respiratory exchange ratio (RER), indicating increased lipid oxidation which therefore supported the finding that 12,13-diHOME increased fatty acid oxidation in vivo (FIG. 3C). The decrease in RER was independent of any change in energy expenditure (FIG. 3D).

To determine whether the effects on fatty acid uptake and oxidation were cell autonomous and specific to skeletal muscle cells, the effects of 12,13-diHOME incubation on the uptake of radiolabeled palmitate in differentiated C2C12 myotubes and 3T3-L1 white adipocytes was determined. Consistent with the in vivo data, the data indicated that there was a significant increase in fatty acid uptake (FIG. 3E) and oxidation (FIG. 3F) in C2C12 cells. 12,13-diHOME did not increase fatty acid uptake or oxidation in 3T3-L1 cells, indicating that 12,13-diHOME did not upregulate lipid metabolism in white adipocytes (FIGS. 3G and 3H). The mechanism for the increase in fatty acid uptake and oxidation in skeletal muscle and in cells was not known, but it was likely that 12,13-diHOME activated signaling pathways leading to translocation of fatty acid transporters.

Figure 4A:
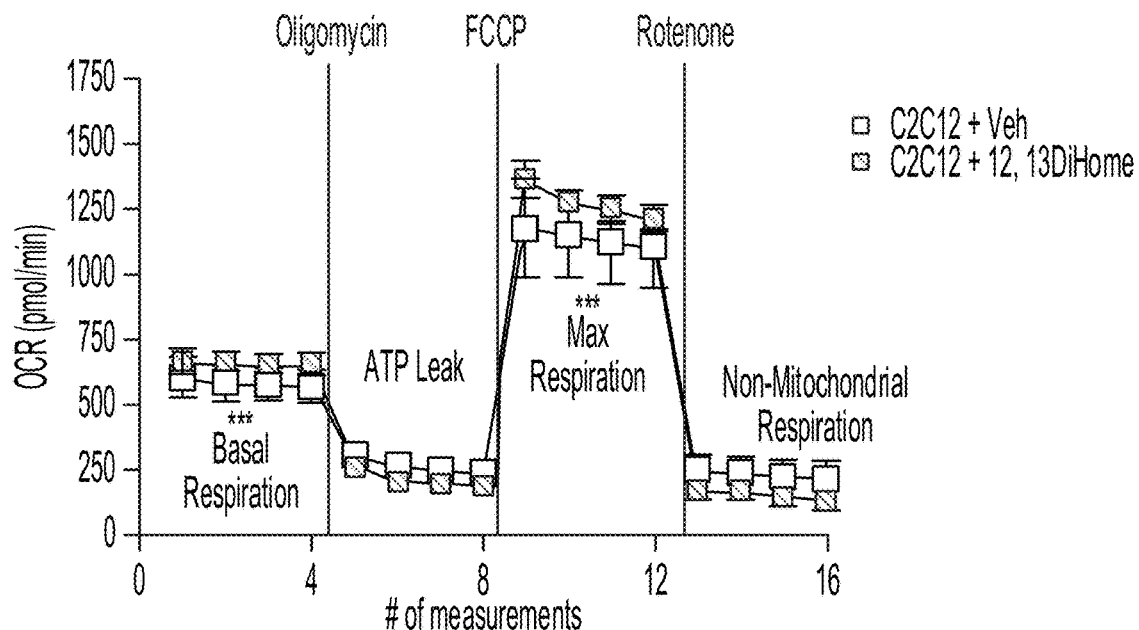
FIGS. 4A-4I depict the results of studies demonstrating 12,13-diHOME increases respiration in skeletal muscle.
Figure 4B:
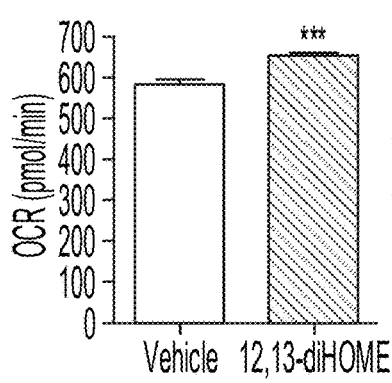
Figure 4C:
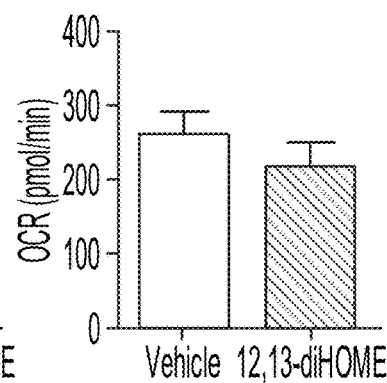
Figure 4D:
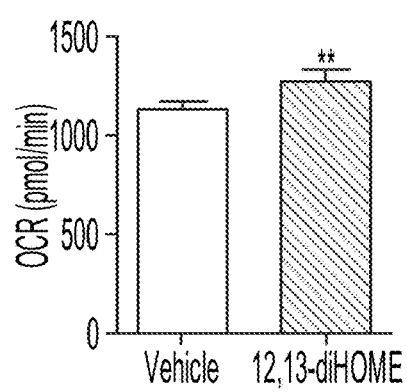

Example 7. Analysis to Determine Whether 12,13-diHOME Increases Mitochondrial Respiration in Muscle Cells To determine if 12,13-diHOME regulated mitochondrial function in muscle, differentiated C2C12 myotubes were incubated with 12,13-diHOME and then analyzed for mitochondrial respiration. 12,13-diHOME incubation increased basal oxygen consumption rate (OCR) and respiratory capacity in C2C12 cells (FIGS. 4A and 4B). 12,13-diHOME did not affect ATP turnover (FIGS. 4A and 4C), but did increase maximal uncoupled respiration (FIGS. 4A and 4D). In 3T3-L1 cells, 12,13-diHOME did not increase OCR under any condition (data not shown).

Figure 4E:

Example 8. Determination of the Function and Mechanism of Increased 12,13-diHOME with Exercise Training These data supported the concept that an increase in 12,13-diHOME after acute exercise functioned to regulate fatty acid uptake and metabolism. Therefore, an analysis of sham and iBAT-mice was performed to determine whether increased 12,13-diHOME with training regulated fat utilization in vivo. Sham and iBAT-mice were sedentary or exercise trained for 3 weeks and subsequently, the RER was measured in metabolic cages. RER was significantly reduced in the sham-trained mice compared to the sham-sedentary mice. In contrast, there was no effect of exercise training on RER in the iBAT-mice. However, when the trained iBAT-mice were treated with 12,13-diHOME, the data demonstrated that RER was significantly decreased (FIG. 4E). These data indicated an essential role for 12,13-diHOME in the regulation of fatty acid metabolism with exercise training.

To identify a mechanism for increased fat utilization with 12,13-diHOME in skeletal muscle, assays were performed to determine the effects of injecting mice with 12,13-diHOME in vivo on the expression of mitochondrial and fatty acid oxidation genes in tibialis anterior muscle. 12,13-diHOME increased expression of several genes involved in mitochondrial activity and biogenesis (citrate synthase, Nrf1, Nrf2), and fatty acid uptake (Cd36, Fatp4) (FIG. 6B). The data also demonstrated that 12,13-diHOME also increased expression of Nrf1 and Nrf2 in the heart (FIG. 6C). However, there was no effect of 12,13-diHOME on mitochondrial or fatty acid oxidation genes in scWAT, pgWAT, liver, or BAT (FIGS. 6D-6G). These findings were consistent with the data showing that 12,13-diHOME regulates fatty acid metabolism in skeletal muscle.

Figure 4F:
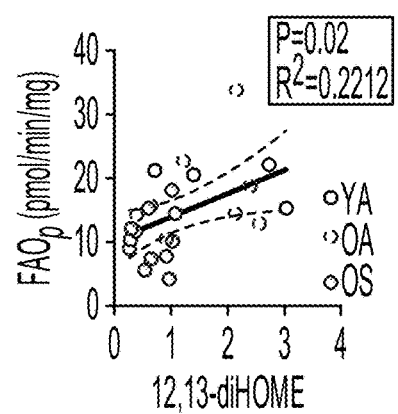
Figure 4G:
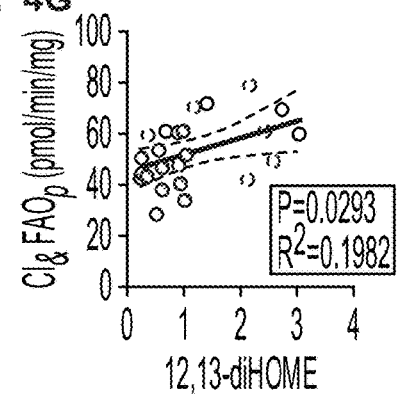
Figure 4H:
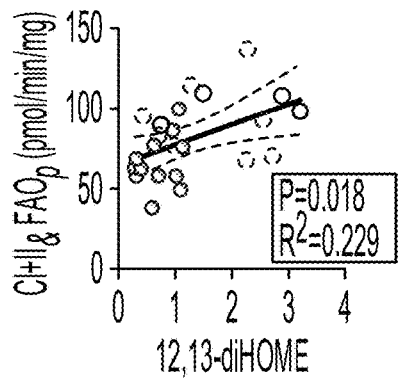
Figure 4I:
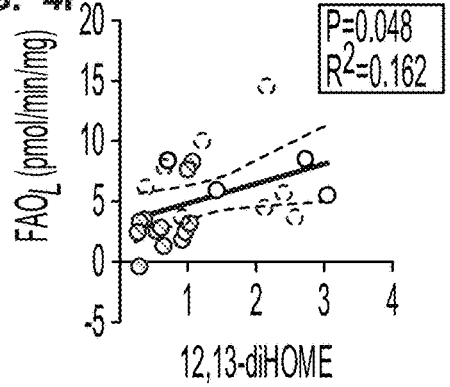

Example 9. Determination of Whether 12,13-diHOME Correlates to Greater Skeletal Muscle Respiration in Humans Studies were performed to determine whether 12,13-diHOME correlated with mitochondrial respiration in permeabilized fiber bundles from vastus lateralis biopsy specimens from human subjects (Cohort 1). ADP stimulated respiration ($FAO_P$) in the presence of palmitoylcarnitine/malate (PCM), maximal complex 1 and $FAO_P$ respiration ($CI\&FAO_P$), and maximal complex I, II and $FAO_P$ respiration ($CI+II_\&FAO_P$) were significantly correlated to circulating 12,13-diHOME (FIGS. 4F-4H). Non-ADP stimulated respiration ($FAO_L$), was also significantly correlated to 12,13-diHOME (FIG. 4I). These data indicated that circulating 12,13-diHOME correlated with increased capacity for mitochondrial respiration in skeletal muscle. Together with the finding that 12,13-diHOME increased maximal respiratory capacity of the C2C12 myotubes, these data raised the possibility that increases in circulating 12,13-diHOME with exercise functioned to facilitate an increase in the respiratory capacity of a working skeletal muscle and may enhance exercise capacity.

Figure 7A:
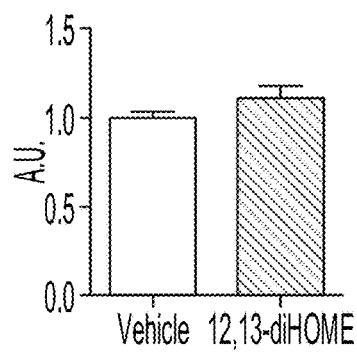
FIGS. 7A-7C shows that 12,13-diHOME does not affect glucose uptake into skeletal muscle.
Figure 7B:
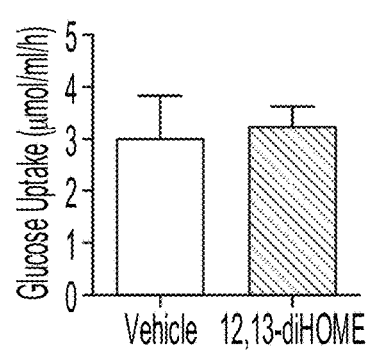
Figure 7C:
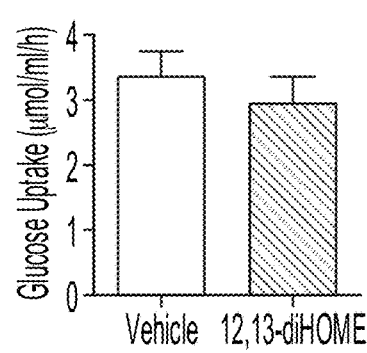

Example 10. Determination of Whether 12,13-diHOME Affected Skeletal Muscle Glucose Uptake Glucose is an important fuel source utilized during exercise. Accordingly, assays were performed to determine whether 12,13-diHOME increased glucose uptake in skeletal muscle. In contrast to the effects of 12,13-diHOME on increasing fatty acid uptake and oxidation in C2C12 myotubes, the data demonstrated that 12,13-diHOME did not affect glucose uptake in these cells (FIG. 7A). To confirm these findings, isolated mouse soleus and extensor digitorum longus (EDL) skeletal muscles were incubated with either vehicle or 12,13-diHOME for 1 hour. The data demonstrated that there was no effect of 12,13-diHOME on the rates of glucose uptake in either muscle (FIGS. 7B and 7C). The findings that 12,13-diHOME regulated fatty acid uptake and oxidation, but not glucose uptake, were interesting and surprising in view of data demonstrating that 12,13-diHOME correlated with circulating triglycerides, but not with circulating glucose levels in human subjects (FIGS. 5F and 5G).

Collectively, these data identified 12,13-diHOME as a circulating lipokine released during moderate intensity exercise in humans and mice. In human subjects, the increase in 12,13-diHOME after acute exercise was demonstrated regardless of age, gender, activity levels, BMI or fat mass. Baseline 12,13-diHOME was higher in physically active subjects compared to sedentary subjects, although this comparison was made in male subjects and cannot necessarily be generalized to females. The correlation analyses suggested that the relationship between 12,13-diHOME and both activity and fitness level was driven by the fat mass of the subjects.

The mouse experiments demonstrated that the tissue source for an increase in 12,13-diHOME with a single bout of exercise is iBAT, and that an increase in 12,13-diHOME increases fatty acid uptake in skeletal muscle in vivo. Importantly, a direct role of 12,13-diHOME for mediating exercise-induced changes in RER and fatty acid oxidation was determined in a mouse model. In the absence of BAT (iBAT-), there was no training effect of RER determined. However, when iBAT-mice were treated with 12,13-diHOME, their RER decreased to the level of exercise-trained mice, indicating an essential role for 12,13-diHOME to contribute, at least in part, to the metabolic response to exercise.

The results here demonstrated that the only linoleic acid metabolite that increased with moderate intensity exercise was 12,13-diHOME. The data provided here suggested that 12,13-diHOME may function specifically in skeletal muscle to increase fatty acid uptake and oxidation and mitochondrial activity.

A recent study investigated the effects of cold exposure on BAT and identified 12,13-diHOME as a metabolite elevated in response to both short term (1 h) and chronic (7-11 days) cold exposure in rodents and humans (Lynes et al., 2017). In the foregoing study, it was demonstrated that 12,13-diHOME is a cold-induced lipokine released from BAT and functions to decrease circulating triglycerides and promote fatty acid uptake specifically in BAT. The parallels between the effects of exercise and cold exposure on 12,13-diHOME were striking but surprising. First, both short term and chronic treatments with these stimuli increased circulating 12,13-diHOME to similar concentrations. In addition, both cold exposure and a single bout of exercise increased 12,13-diHOME in BAT, which was considered to be the tissue source of circulating 12,13-diHOME. This was surprising because while cold exposure is a well-known and potent stimulator of BAT activity, most investigations have shown that exercise training decreases BAT activity in humans and rodents (Motiani et al., 2017; Vosselman et al., 2015; Wu et al., 2014). However, it appears that cold exposure causes the release of 12,13-diHOME from BAT to function in an autocrine manner to provide fuel for the BAT, whereas the data disclosed herein indicated that exercise causes the release of 12,13-diHOME from BAT to function in an endocrine manner, resulting in stimulation of fatty acids into the working skeletal muscle.

In sum, these data provided a previously unidentified role for BAT in the metabolic response to exercise and the first evidence that BAT-derived molecules, including signaling lipids, can increase fatty acid oxidation and uptake in skeletal muscle.

| Key Resources Table | | |
|---|---|---|
| REAGENT or RESOURCE | SOURCE | IDENTIFIER |
| Biological Samples | | |
| Human Tissue Samples | herein | N/A |
| Human Tissue Samples | (Lynes et al., 2017) | N/A |
| Chemicals, Peptides, and Recombinant Proteins | | |
| FFA-SS-Luc | Intrace Medical | N/A |
| 12,13-diHOME | Cayman Chemical | Cat#10009832 |
| Critical Commercial Assays | | |
| Triglycerides Assay Kit | Roche | COBAS INTEGRA TRIGL, test ID 0-010 |
| Glucose Assay Kit | Roche | COBAS INTEGRA Glucose HK Gen.3 |
| Experimental Models: Cell Lines | | |
| C2C12 Cells | ATCC | Cat # CRL-1772 |
| 3T3-L1 Cells | ATCC | Cat # CL-173 |

Key Resources Table

| REAGENT or RESOURCE | SOURCE | IDENTIFIER |
|---|---|---|
| Experimental Models: Organisms/Strains | | |
| Mouse: C57BL/6 | Charles River Laboratories | Strain code: 027 |
| Mouse: ACTA1cre+/− | The Jackson Laboratory | Stock no. 006139 |
| Mouse: Rosa(stop)Luc+/+ | The Jackson Laboratory | Stock no. 005125 |
| Mouse: CD-1 IGS | Charles River Laboratories | Strain code: 022 |
| Oligonucleotides | | |
| A full list of Primers is in Table 4 | herein | N/A |
| Software and Algorithms | | |
| GraphPad Prism 7 | GraphPad Software | N/A |
| Image J Java 1.6.0_2.4 | NIH | N/A |
| Living Image Software (IVIS Imaging Systems) | Perkin Elmer | N/A |

TABLE 4

Primer sets used in this study

| Primer | Sequence | SEQ ID NO: |
|---|---|---|
| Ephx1 F | GGAGACCTTACCACTTGAAGATG | 1 |
| Ephx1 R | GCCCGGAACCTATCTATCCTCT | 2 |
| Ephx2 F | ACCACTCATGGATGAAAGCTACA | 3 |
| Ephx2 R | TCAGGTAGATTGGCTCCACAG | 4 |
| Ephx3 F | CAGTGGACTCCGATAGCACG | 5 |
| Ephx3 R | TGGGACGACTACAGAGCCG | 6 |
| Ephx4 F | TCCCTGGTGTACGGCTACTG | 7 |
| Ephx4 R | ATCTTAACCCGGAGTCCTTGA | 8 |
| GAPDH F | AACTTTGGCATTGTGGAAGG | 9 |
| GAPDH R | ACACATTGGGGGTAGGAACA | 10 |
| Cs F | GACTACATCTGGAACACACTCAATTCA | 11 |
| Cs R | CGAGGGTCAGTCTTCCTCAGTAC | 12 |
| Nrf1 F | CAACAGGGAAGAAACGGAAA | 13 |
| Nrf1 R | GCACCACATTCTCCAAAGGT | 14 |
| Nrf2 F | AGGTTGCCCACATTCCCAAACAAG | 15 |
| Nrf2 R | TTGCTCCATGTCCTGCTCTATGCT | 16 |
| Tfam F | GTCCATAGGCACCGTATTGC | 17 |
| Tfam R | CCCATGCTGGAAAAACACTT | 18 |
| Pgc1a F | GAATCAAGCCACTACAGACACCG | 19 |
| Pgc1a R | CATCCCTCTTGAGCCTTTCGTG | 20 |
| Cd36 F | TGGAGCTGTTATTGGTGCAG | 21 |
| Cd36 R | TGGGTTTTGCACATCAAAGA | 22 |
| Fatp1 F | TGCCACAGATCGGCGAGTTCTA | 23 |
| Fatp1 R | AGTGGCTCCATCGTGTCCTCAT | 24 |
| Fatp4 F | GACTTCTCCAGCCGTTTCCACA | 25 |
| Fatp4 R | CAAAGGACAGGATGCGGCTATTG | 26 |

REFERENCES

Beltz, N. M., Gibson, A. L., Janot, J. M., Kravitz, L., Mermier, C. M., and Dalleck, L. C. (2016). Graded Exercise Testing Protocols for the Determination of VO2max: Historical Perspectives, Progress, and Future Considerations. Journal of sports medicine (Hindawi Publishing Corporation) 2016, 3968393.

Bruce, R. A. (1971). Exercise testing of patients with coronary heart disease. Principles and normal standards for evaluation. Annals of clinical research 3, 323-332.

Burhans, M. S., Flowers, M. T., Harrington, K. R., Bond, L. M., Guo, C. A., Anderson, R. M., and Ntambi, J. M. (2015). Hepatic oleate regulates adipose tissue lipogenesis and fatty acid oxidation. Journal of lipid research 56, 304-318.

Cao, H., Gerhold, K., Mayers, J. R., Wiest, M. M., Watkins, S. M., and Hotamisligil, G. S. (2008). Identification of a lipokine, a lipid hormone linking adipose tissue to systemic metabolism. Cell 134, 933-944.

Carnero, E. A., Dubis, G. S., Hames, K. C., Jakicic, J. M., Houmard, J. A., Coen, P. M., and Goodpaster, B. H. (2017). Randomized trial reveals that physical activity and energy expenditure are associated with weight and body composition after RYGB. Obesity (Silver Spring).

Coen, P. M., Jubrias, S. A., Distefano, G., Amati, F., Mackey, D. C., Glynn, N. W., Manini, T. M., Wohlgemuth, S. E., Leeuwenburgh, C., Cummings, S. R., et al. (2013). Skeletal muscle mitochondrial energetics are associated with maximal aerobic capacity and walking speed in older adults. The journals of gerontology. Series A, Biological sciences and medical sciences 68, 447-455.

Coen, P. M., Menshikova, E. V., Distefano, G., Zheng, D., Tanner, C. J., Standley, R. A., Helbling, N. L., Dubis, G. S., Ritov, V. B., Xie, H., et al. (2015). Exercise and Weight Loss Improve Muscle Mitochondrial Respiration, Lipid Partitioning and Insulin Sensitivity Following Gastric Bypass Surgery. Diabetes.

Egan, B., and Zierath, J. R. (2013). Exercise metabolism and the molecular regulation of skeletal muscle adaptation. Cell metabolism 17, 162-184.

Goodyear, L. J., and Kahn, B. B. (1998). Exercise, glucose transport, and insulin sensitivity. Annual review of medicine 49, 235-261.

Hayashi, T., Hirshman, M. F., Kurth, E., Winder, W. W., and Goodyear, L. J. (1998). Evidence for 5' AMP-activated protein kinase mediation of the effect of muscle contraction on glucose transport. Diabetes 47, 1369-1373.

Henkin, A. H., Cohen, A. S., Dubikovskaya, E. A., Park, H. M., Nikitin, G. F., Auzias, M. G., Kazantzis, M., Bertozzi, C. R., and Stahl, A. (2012). Real-time non-invasive imaging of fatty acid uptake in vivo. ACS chemical biology 7, 1884-1891.

Liao, J., Sportsman, R., Harris, J., and Stahl, A. (2005). Real-time quantification of fatty acid uptake using a novel fluorescence assay. Journal of lipid research 46, 597-602.

Liu, S., Brown, J. D., Stanya, K. J., Homan, E., Leidl, M., Inouye, K., Bhargava, P., Gangl, M. R., Dai, L., Hatano, B., et al. (2013). A diurnal serum lipid integrates hepatic lipogenesis and peripheral fatty acid use. Nature 502, 550-554.

Lynes, M. D., Leiria, L. O., Lundh, M., Bartelt, A., Shamsi, F., Huang, T. L., Takahashi, H., Hirshman, M. F., Schlein, C., Lee, A., et al. (2017). The cold-induced lipokine 12,13-diHOME promotes fatty acid transport into brown adipose tissue. Nature medicine 23, 631-637.

Motiani, P., Virtanen, K. A., Motiani, K. K., Eskelinen, J. J., Middelbeek, R. J., Goodyear, L. J., Savolainen, A. M., Kemppainen, J., Jensen, J., Din, M. U., et al. (2017). Decreased insulin-stimulated brown adipose tissue glucose uptake after short-term exercise training in healthy middle-aged men. Diabetes, obesity & metabolism.

Nedachi, T., and Kanzaki, M. (2006). Regulation of glucose transporters by insulin and extracellular glucose in C2C12 myotubes. American journal of physiology. Endocrinology and metabolism 291, E817-828.

Nieman, D. C., Shanely, R. A., Luo, B., Meaney, M. P., Dew, D. A., and Pappan, K. L. (2014). Metabolomics approach to assessing plasma 13- and 9-hydroxy-octadecadienoic acid and linoleic acid metabolite responses to 75-km cycling. American journal of physiology. Regulatory, integrative and comparative physiology 307, R68-74.

Pedersen, B. K., and Febbraio, M. A. (2008). Muscle as an endocrine organ: focus on muscle-derived interleukin-6. Physiological reviews 88, 1379-1406.

Powell, W. S. (1999). Extraction of eicosanoids from biological fluids, cells, and tissues. Methods in molecular biology (Clifton, N.J.) 120, 11-24.

Pruchnic, R., Katsiaras, A., He, J., Kelley, D. E., Winters, C., and Goodpaster, B. H. (2004). Exercise training increases intramyocellular lipid and oxidative capacity in older adults. American journal of physiology. Endocrinology and metabolism 287. E857-862.

Sisemore. M. F., Zheng, J., Yang, J. C., Thompson, D. A., Plopper, C. G., Cortopassi, G. A., and Hammock, B. D. (2001). Cellular characterization of leukotoxin diol-induced mitochondrial dysfunction. Archives of biochemistry and biophysics 392, 32-37.

Stanford, K. I., and Goodyear, L. J. (2016). Exercise regulation of adipose tissue. Adipocyte 5, 153-162.

Stanford, K. I., Middelbeek, R. J., and Goodyear, L. J. (2015a). Exercise Effects on White Adipose Tissue: Beiging and Metabolic Adaptations. Diabetes 64, 2361-2368.

Stanford. K. I., Middelbeek, R. J., Townsend, K. L., Lee, M. Y., Takahashi, H., So, K., Hitchcox. K. M., Markan, K. R., Hellbach, K., Hirshman, M. F., et al. (2015b). A novel role for subcutaneous adipose tissue in exercise-induced improvements in glucose homeostasis. Diabetes 64, 2002-2014.

Townsend, K. L., An, D., Lynes. M. D., Huang, T. L., Zhang, H., Goodyear, L. J., and Tseng. Y. H. (2013). Increased mitochondrial activity in BMP7-treated brown adipocytes, due to increased CPT1- and CD36-mediated fatty acid uptake. Antioxidants & redox signaling 19, 243-257.

Vernochet, C., Mourier, A., Bezy, O., Macotela, Y., Boucher, J., Rardin, M. J., An, D., Lee, K. Y., Ilkayeva, O. R., Zingaretti, C. M., et al. (2012). Adipose-specific deletion of TFAM increases mitochondrial oxidation and protects mice against obesity and insulin resistance. Cell metabolism 16, 765-776.

Vosselman, M. J., Hocks, J., Brans. B., Pallubinsky, H., Nascimento, E. B., van der Lans, A. A., Broeders, E. P., Mottaghy, F. M., Schrauwen, P., and van Marken Lichtenbelt, W. D. (2015). Low brown adipose tissue activity in endurance-trained compared with lean sedentary men. International journal of obesity (2005).

Wu, M. V., Bikopoulos, G., Hung, S., and Ceddia, R. B. (2014). Thermogenic capacity is antagonistically regulated in classical brown and white subcutaneous fat depots by high fat diet and endurance training in rats: impact on whole-body energy expenditure. The Journal of biological chemistry 289, 34129-34140.

---

We claim:

1. A method of treating a human subject having a mitochondrial disorder or reducing severity of a symptom in a human subject having a mitochondrial disorder, said method comprising administering an effective amount of 12,13-dihydroxy-9Z-octadecenoic acid (12,13-diHOME), a stereoisomer, a geometric isomer, or a pharmaceutically acceptable salt thereof, to a subject having a mitochondrial disorder, wherein the mitochondrial disorder is selected from the group consisting of diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), neuropathy, dementia, mitochondrial myopathy, myoclonic epilepsy with ragged red fibers (MERRF), progressive myoclonic epilepsy, mitochondrial myopathy, encephalomyopathy, lactic acidosis, stroke-like symptoms (MELAS), and mitochondrial neurogastrointestinal encephalomyopathy (MNGIE).

2. The method of claim 1, wherein the symptom of the mitochondrial disorder is selected from the group consisting of poor growth, loss of muscle coordination, muscle weakness, visual and hearing problems, learning disabilities, heart disease, liver disease, kidney disease, gastrointestinal disorders, respiratory disorders, neurological problems, autonomic dysfunction and dementia.

3. A method of treating a human subject having a condition associated with mitochondrial dysfunction, said method comprising administering an effective amount of 12,13-dihydroxy-9Z-octadecenoic acid (12,13-diHOME), a stereoisomer, a geometric isomer, or a pharmaceutically acceptable salt thereof, to a subject having Huntington's disease, Alzheimer's disease, Parkinson's disease, bipolar disorder, schizophrenia, aging and senescence, anxiety disorders, cardiovascular disease, cancer, diabetes, sarcopenia, or chronic fatigue syndrome; and wherein the effective amount of 12,13-diHOME is about 0.5 mg/kg to about 100 mg/kg.

4. The method of claim 3, wherein the subject has type 2 diabetes.

5. The method of claim 3, wherein the subject has cardiovascular disease.

6. The method of claim 3, wherein the subject has sarcopenia.

7. A method of treating a human subject having hypertriglyceridemia, said method comprising administering an effective amount of 12,13-diHOME, a stereoisomer, a geometric isomer, or a pharmaceutically acceptable salt thereof, to a subject having hypertriglyceridemia, wherein the effective amount of 12,13-diHOME is about 0.5 mg/kg to about 100 mg/kg.

8. A method of treating a human subject having a disorder that would benefit from an increased level of metabolic activity, said method comprising administering an effective amount of 12,13-dihydroxy-9Z-octadecenoic acid (12,13-diHOME), a stereoisomer, a geometric isomer, or a pharmaceutically acceptable salt thereof, to a subject having obesity or type 2 diabetes; and wherein the effective amount of 12,13-diHOME is about 0.5 mg/kg to about 100 mg/kg.

* * * * *